(12) United States Patent
Skaling et al.

(10) Patent No.: US 7,631,545 B2
(45) Date of Patent: Dec. 15, 2009

(54) JET-ACTION PLUNGER-BASED TENSIOMETER APPARATUS

(75) Inventors: Whitney Skaling, Buellton, CA (US); Percy Skaling, Santa Barbara, CA (US)

(73) Assignee: SoilMoisture Equipment Corporation, Goleta, CA (US)

( * ) Notice: Subject to any disclaimer, the term of this patent is extended or adjusted under 35 U.S.C. 154(b) by 282 days.

(21) Appl. No.: 11/743,245

(22) Filed: May 2, 2007

(65) Prior Publication Data

US 2008/0271521 A1    Nov. 6, 2008

(51) Int. Cl.
  *G01N 25/56* (2006.01)
  *G01N 19/10* (2006.01)
  *A01G 27/00* (2006.01)
(52) U.S. Cl. .............................. 73/73; 137/78.3; 239/63
(58) Field of Classification Search ...................... 73/73; 239/63; 137/78.3
  See application file for complete search history.

(56) References Cited

U.S. PATENT DOCUMENTS

| | | | |
|---|---|---|---|
| 2,878,671 A * | 3/1959 | Prosser et al. .................. 73/73 |
| 3,898,872 A | 8/1975 | Skaling et al. | |
| 4,068,525 A * | 1/1978 | Skaling .......................... 73/73 |
| 4,548,225 A * | 10/1985 | Busalacchi ...................... 73/73 |
| 4,938,248 A * | 7/1990 | Browne ...................... 137/78.3 |
| 5,113,888 A * | 5/1992 | Beggs ........................ 137/78.3 |
| 5,156,179 A * | 10/1992 | Peterson et al. ............ 137/78.3 |
| 6,782,909 B1 * | 8/2004 | Ragless ...................... 137/78.3 |

\* cited by examiner

*Primary Examiner*—Lisa M Caputo
*Assistant Examiner*—Punam Patel
(74) *Attorney, Agent, or Firm*—Lyon & Harr, LLP; Richard T. Lyon

(57) ABSTRACT

The present invention is embodied in a tensiometer apparatus and process that employs novel techniques for performing the required routine service operation of refilling a sealable measurement chamber of the apparatus with liquid from a reservoir using a novel, piston-type, "jet-action" plunger mechanism. These novel techniques result in a tensiometer which is easier to use, requires no tools for assembly or replacement of parts, and is easier and lower cost to manufacture and maintain. These novel techniques also result in a tensiometer which has improved measurement sensitivity and accuracy, higher reliability and a longer operating lifetime than conventional tensiometers.

12 Claims, 15 Drawing Sheets

JET-ACTION PLUNGER-BASED TENSIOMETER APPARATUS

BACKGROUND

Moisture measuring apparatus commonly known as tensiometers are used to measure the moisture content of soil and other like medium, and have been in use for some time. Tensiometers are commonly used by farmers and others responsible for managing soil irrigation, to monitor the moisture content of the soil and determine when it is necessary to water the soil and how much water should be applied. Using a tensiometer in this fashion a farmer can control the irrigation schedule for the soil on an ongoing basis, in conjunction with changes in weather and season, in order to optimize plant growth. Tensiometers are also commonly used in the scientific study of soils and plants.

A tensiometer generally includes a measurement tube whose interior provides a sealable measurement chamber, a porous tip attached to the bottom end of the tube, and a vacuum gauge connected to the chamber at the top end of the tube. The chamber is first filled with water and then sealed. The porous tip is then buried in the soil, thus establishing liquid contact between the water in the chamber and films of moisture in the soil surrounding the porous tip. Via the general process of capillary action, relatively dry soil tends to pull water from the chamber through the porous tip into the soil. However, since the chamber is sealed, only a small amount of water is pulled into the soil. The pulling effect of the dryer soil creates a negative pressure and related vacuum in the chamber, which can be measured on the gauge. As water is pulled out of the soil surrounding the tensiometer by evaporation and plants in the soil, more water is pulled from the chamber into the soil. Soil with relatively high moisture content, such as after rain or watering, pulls less water from the chamber, resulting in a lower negative pressure and related vacuum in the chamber, and a correspondingly lower reading on the gauge.

As stated previously, a small amount of water in the tensiometer's measurement chamber is lost over a period of time. Thus, air tends to accumulate in the chamber. The air may also initially be present, in dissolved form, in the water inside the chamber. The relatively low pressure in the chamber allows the air to come out of solution, resulting in the air gradually accumulating both on the chamber wall and at the top of the chamber. Air may also enter the chamber from the surrounding soil by diffusion through the porous tip. This accumulation of air in the chamber results in a reduction in the tensiometer's measurement sensitivity to changes in the moisture content of the soil. The end result is a degradation of the tensiometer's measurement accuracy. In order to address this problem and maintain the tensiometer's measurement sensitivity and accuracy, the tensiometer must be routinely serviced by adding water to the chamber to remove the accumulated air.

In some types of conventional tensiometers the accumulated air is removed from the measurement chamber by first manually removing a seal on the top of the chamber, then manually pouring more water into the chamber to refill it with water, and then manually installing the seal back onto the chamber. In addition to the inconvenience of this method, it is disadvantageous for a number of other reasons. For example, the aforementioned water refill operation is required to be performed routinely in order to maintain the tensiometer's measurement sensitivity and accuracy. However, during the period of time that the seal is removed, the vacuum in the chamber is lost, resulting in water flowing out of the chamber through the porous tip and into the surrounding soil. A long time may be required to pass before this local accumulation of water in the soil surrounding the tip disperses enough to allow the tensiometer to perform an accurate reading of the overall moisture content in the soil. Furthermore, the act of manually pouring more water into the chamber to refill it may not dislodge all the air bubbles that have accumulated on the wall of the chamber, especially for smaller diameter chambers. Hence, even after the chamber has been refilled with water, some air can be left in the chamber. Finally, installing the seal back onto the chamber asserts a positive pressure on the water in the chamber, which causes even more water to flow out of the chamber into the soil and further degrades the tensiometer's measurement sensitivity and accuracy.

Other types of conventional tensiometers contain a water reservoir connected to the measurement chamber through a valve which can be manually operated to allow water to flow into the chamber to refill it. However, these types of tensiometers generally also possess the aforementioned disadvantages in varying degrees.

SUMMARY

The present invention is directed toward a tensiometer apparatus and process for measuring the moisture content of soil and other like medium which addresses the disadvantages of conventional tensiometers and in general, significantly advances the state of the art of tensiometers. It should be noted that the use of the terms "seal," "sealed" and "sealably" hereinafter are intended to imply an airtight seal which is capable of maintaining a vacuum.

The present invention is embodied in a tensiometer apparatus and process that employs novel techniques for performing the required routine service operation of refilling a sealable measurement chamber of the apparatus with liquid from a reservoir using a novel, spring-loaded, piston-type, "jet-action" plunger mechanism. These novel techniques have a number of advantages over conventional tensiometers including but not limited to the following. The chamber's seal is removed for only a minimal period of time and the chamber is quickly re-sealed without positive pressure being applied to the chamber, so that the unwanted flow out of the chamber into the surrounding soil during the refill operation is minimized. The refill operation is also much easier and faster since the operator simply has to manually depress and release a plunger assembly contained within the tensiometer. Air which has accumulated over time and is entrapped in the chamber is more effectively removed during the refill operation, even for a chamber with a relatively small diameter. The overall structure and design of the tensiometer apparatus is simple and has few parts. Finally, the routine chamber refilling service operation is performed without applying torque to the tensiometer and disturbing its liquid contact with the soil. The end result is a tensiometer which is easier to use, requires no tools for assembly or replacement of parts, is easier and lower cost to manufacture and maintain, and has improved measurement sensitivity and accuracy, higher reliability, and longer operating lifetime than conventional tensiometers.

More particularly, in general terms and by way of example but not limitation, the present invention is embodied in a tensiometer apparatus and process that includes the following basic parts. A conventional porous tip is attached to the bottom end of a measurement tube. The interior of the tube provides a sealable measurement chamber. A passageway exists between the bottom of the chamber and the top of the porous tip, allowing liquid to flow out of the chamber into the porous tip. A conventional vacuum gauge is attached to the top end of the tube. A passageway exists between the gauge and the top of the chamber, allowing the gauge to measure the current level of negative pressure and related vacuum in the chamber. A reservoir is also attached to the top end of the tube. A passageway exists between the bottom of the reservoir and the top of the chamber, allowing liquid contained within the reservoir to flow out of the reservoir into the chamber. The top of the reservoir is optionally covered with a cap assembly whose radially inner section includes a flexible membrane. The cap assembly is removed briefly to allow liquid to be added to the reservoir. When the cap assembly is installed on the reservoir it serves to seal the reservoir, preventing contamination and evaporation of the liquid contained therein. The installed cap assembly also provides a secondary seal for the measurement chamber.

Furthermore, in general terms and by way of example but not limitation, in an embodiment of the present invention a spring-loaded, piston-type plunger assembly, hereinafter also simply referred to as a plunger, is slidably and removably fitted inside the reservoir. A valve is located at the bottom of the plunger. A disc is also located on the plunger, above the valve. The disc is oriented perpendicular to the direction in which the plunger slides. When the cap assembly is installed on the reservoir, a small gap exists between an actuating button on the cap assembly's flexible membrane and the top of the plunger, such that the actuating button normally exerts no force onto the top of the plunger. The plunger serves a number of different functions including but not limited to the following. When the plunger is in its normally closed position, the valve at the bottom of the plunger closes and seals the passageway from the reservoir to the chamber, thus providing a primary seal for the chamber. When an operator manually depresses the actuating button, the button comes in contact with the top of the plunger and applies a downward force to the top of the plunger, which causes the plunger and valve to be slidably depressed downward so that the valve opens. This opens the passageway from the reservoir to the chamber and allows liquid contained within the reservoir to flow into the chamber. This flow of liquid into the chamber is accelerated by the disc on the plunger. The relatively large surface area of the disc moves downward in conjunction with the plunger, serving to forcibly pump a relatively large volume of liquid into the chamber via what is hereinafter termed "jet-action." This jet-action flow of liquid into the chamber serves to purge practically all of the air which has accumulated in the chamber over time, including but not limited to air bubbles both on the chamber wall and at the top of the chamber, by forcibly sweeping the bubbles away. When the operator releases the actuating button, the plunger's disc and valve move upward in a return stroke until the valve reaches its normally closed position and there is once again a small gap between the button and the top of the plunger. The return stroke of the disc creates a partial vacuum and related negative pressure in the chamber which causes air bubbles remaining in the chamber to expand, thus further purging the chamber of air remaining therein by causing at least some of the bubbles remaining on the chamber wall to break loose from the wall and be drawn into the reservoir. When the plunger completes its return stroke and the valve reaches its normally closed position, the passageway from the reservoir to the chamber is closed and the chamber is re-sealed without applying positive pressure to the chamber.

It should be noted that while the foregoing limitations in existing tensiometers described in the Background section can be resolved by a particular implementation of a jet-action plunger-based tensiometer apparatus and process according to the present invention, this is in no way limited to implementations that just solve any or all of the noted disadvantages. Rather, the present apparatus and process have a much wider application as will become evident from the descriptions to follow.

It should also be noted that this Summary is provided to introduce a selection of concepts, in a simplified form, that are further described below in the Detailed Description. This Summary is not intended to identify key features or essential features of the claimed subject matter, nor is it intended to be used to determine or limit the scope of the claimed subject matter. In addition to the just described features and benefits, other aspects and advantages of the present invention will become apparent from the detailed description which follows hereinafter when taken in conjunction with the drawing figures which accompany it.

DESCRIPTION OF THE DRAWINGS

The specific features, aspects, and advantages of the present invention will become better understood with regard to the following description, appended claims, and accompanying drawings where:

DETAILED DESCRIPTION

In the following description of embodiments of the present invention reference is made to the accompanying drawings which form a part hereof, and in which are shown, by way of illustration, specific embodiments in which the invention may be practiced. It is understood that other embodiments may be utilized and structural changes may be made without departing from the scope of the present invention.

The present invention is directed toward a tensiometer apparatus and process for measuring the moisture content of soil and other like medium. The present invention is embodied in a tensiometer apparatus and process that employs novel techniques for performing the required routine service operation of refilling a sealable measurement chamber of the apparatus with liquid from a reservoir using a novel, piston-type, "jet-action" plunger mechanism. These techniques, along with the related tensiometer apparatus and process, will now be described in detail.

Figure 1:
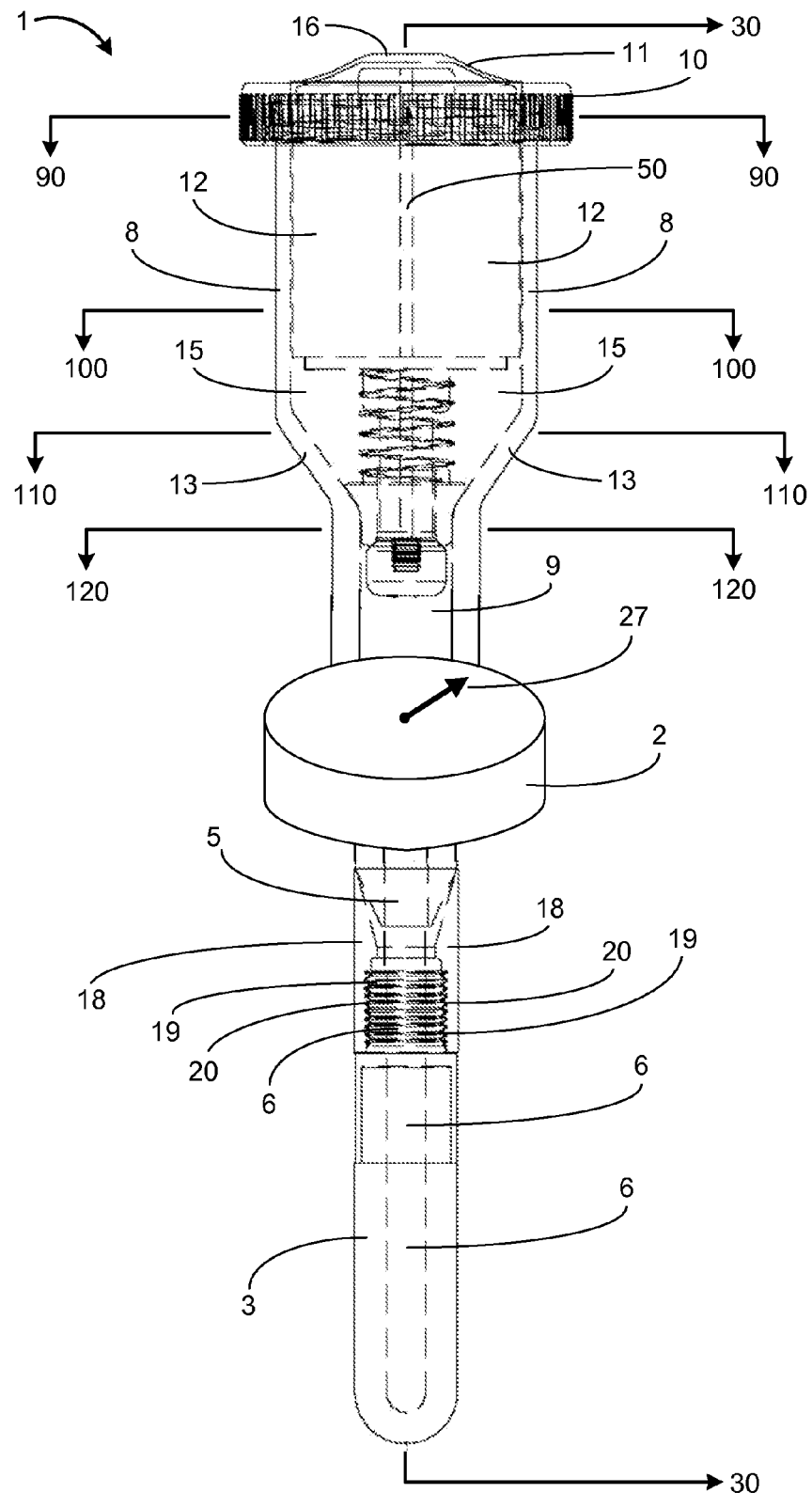
FIG. 1 shows an exemplary transparent longitudinal plan view of a tensiometer apparatus according to the present invention with its valve in a normally closed position.
Figure 2:
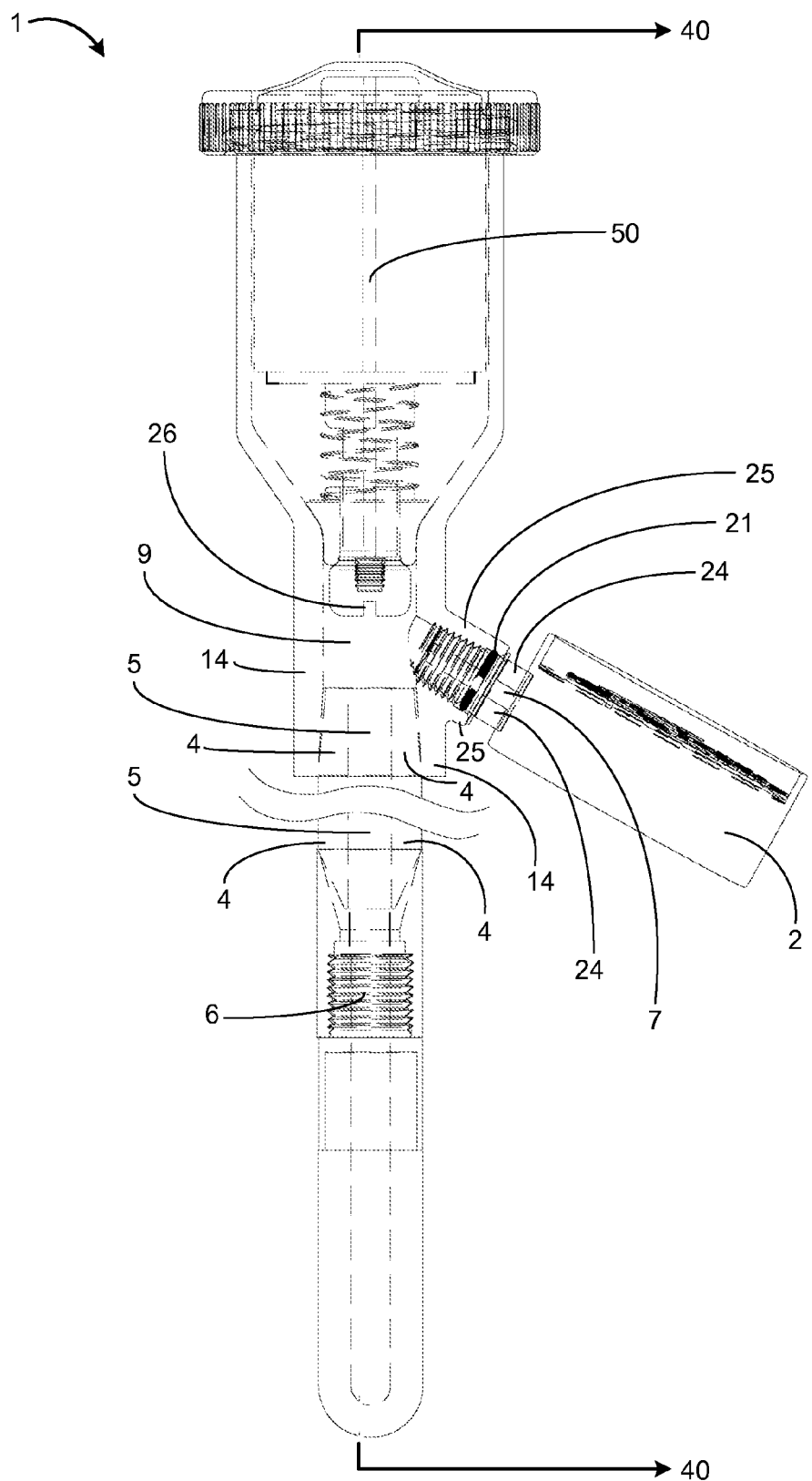
FIG. 2 shows an exemplary transparent longitudinal plan view of the tensiometer apparatus of FIG. 1 rotated counter-clockwise 90 degrees.
Figure 3:
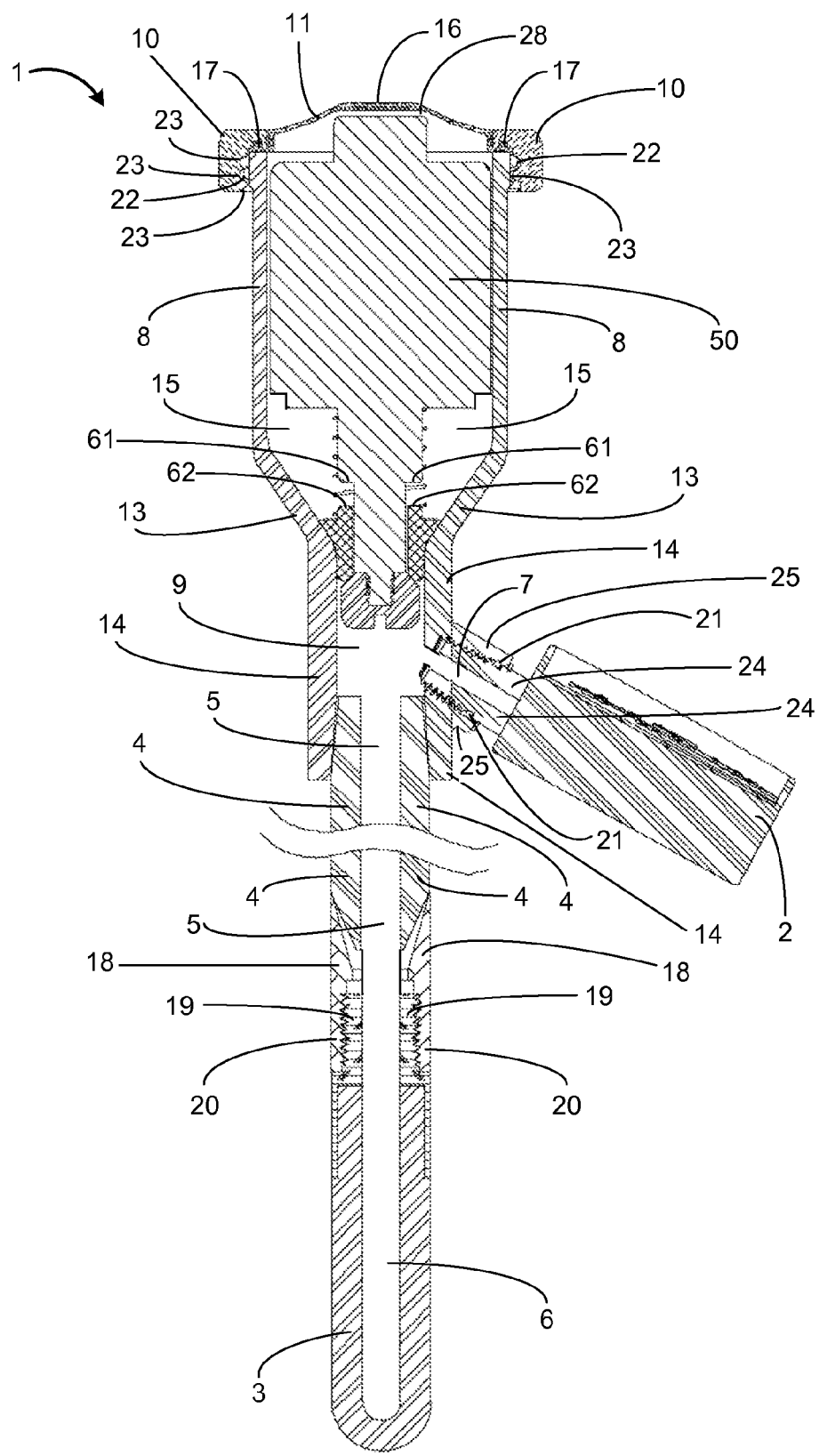
FIG. 3 shows an exemplary cross-sectional longitudinal view of the tensiometer apparatus of the present invention taken along line 30-30 of FIG. 1.
Figure 4:
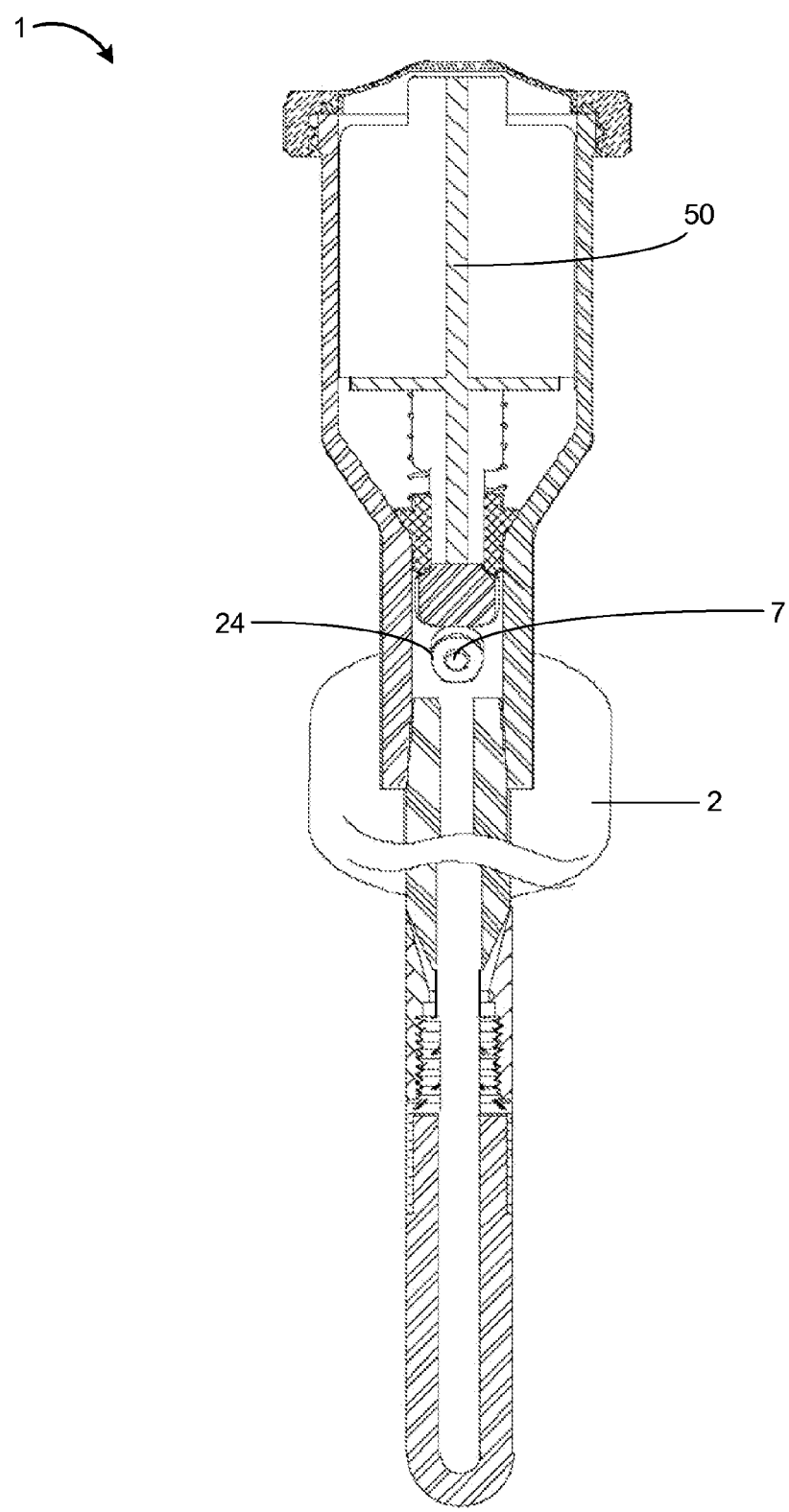
FIG. 4 shows an exemplary cross-sectional longitudinal view of the tensiometer apparatus of the present invention taken along line 40-40 of FIG. 2.

FIGS. 1 and 2 show two different exemplary transparent longitudinal plan views of a summary embodiment of the present tensiometer apparatus 1 with its valve in a normally closed position. More particularly, FIG. 1 shows an exemplary transparent longitudinal plan view of an embodiment of the present tensiometer apparatus 1 with a conventional vacuum gauge 2 on the apparatus pointing toward the viewer. FIG. 2 shows a corresponding exemplary transparent longitudinal plan view of the apparatus 1 of FIG. 1 rotated counterclockwise 90 degrees so that the gauge 2 is pointing to the right of the apparatus. FIG. 3 shows a corresponding exemplary cross-sectional longitudinal view of apparatus 1 taken along line 30-30 of FIG. 1. FIG. 4 shows a corresponding exemplary cross-sectional longitudinal view of apparatus 1 taken along line 40-40 of FIG. 2.

As shown in FIGS. 1-4, the apparatus 1 includes the following parts. The interior of an elongated measurement tube 4 provides an elongated measurement chamber 5 which is sealable as will be described hereinafter. A porous tip 3 is sealably attached to the bottom end of the tube 4 via a coupling adapter 18. In order to facilitate easy servicing and replacement of the tip 3, it is preferable that the method of sealably attaching the tip to the adapter 18 allows the tip to be easily removed from, and installed back onto, the adapter. In the embodiment of the present invention shown in FIGS. 1-4, this is accomplished as follows. The top end 19 of the tip 3 is externally threaded and the bottom end 20 of the coupling adapter 18 includes a mating internally threaded passageway into which the tip's externally threaded top end is installed. When the apparatus 1 is in operational field use, the chamber 5 should be filled with liquid (not shown). The most common type of liquid used is water. However, other types of liquids can also be used based on the type of medium the apparatus 1 is measuring the moisture content of.

Referring again to FIGS. 1-4, a passageway 6 exists between the bottom of the chamber 5 and the top of the tip 3 which allows liquid contained within the chamber to flow out of the chamber into the tip. A cylindrically-shaped reservoir 8/13/14 is sealably attached to the top end of the measurement tube 4. The upper wall 8 of the reservoir forms a cylindrical cavity 12 inside the upper section of the reservoir which holds liquid. The reservoir has a funnel-shaped midsection 13 which forms a funnel-shaped cavity 15. As will be described hereinafter, liquid freely flows from cavity 12 into cavity 15. The reservoir's midsection 13 converges radially inward to a lower tube 14, whose interior forms cylindrically-shaped passageway 9. Various different methods can be used to attach the lower tube 14 to the measurement tube 4 such that a seal is created between the two tubes. In the embodiment of the present invention shown in FIGS. 1-4, the diameter of lower tube 14 is sized such that the measurement tube 4 is snugly fitted into the lower tube and sealably retained in place using glue or any other equivalent method. As will be described hereinafter, passageway 9 allows liquid held in reservoir cavities 12 and 15 to flow out of the reservoir 8/13/14 and into the top of the chamber 5.

Referring yet again to FIGS. 1-4, the top of the reservoir 8 is optionally covered with a cap assembly 10/11/16 which is comprised of a rigid cap ring 10 and a flexible, but relatively stiff, membrane 11, which hereinafter will simply be referred to as a flexible membrane 11. The flexible membrane 11 is sealably attached to the cap ring 10 to form the radially inner section of the cap assembly 10/11/16. The flexible membrane 11 tapers radially upward towards its center to form an actuating button 16, whose function will be described hereinafter. In order to facilitate easy servicing and replacement of the membrane 11, it is preferable that the method of sealably attaching it to the cap ring 10 allows it to be easily removed from and installed back onto the cap ring. In the embodiment of the present invention shown in FIGS. 1-4, the diameter of the flexible membrane 11 is sized such that it extends under a lip 17 of the cap ring 10. The cap assembly 10/11/16 is briefly removed from the reservoir 8 to allow liquid to be added to the reservoir as necessary to refill it. In the embodiment of the present invention shown in FIGS. 1-4, the top 22 of the reservoir 8 is externally threaded and the cylindrical surface 23 on the inside of the cap ring 10 is internally threaded in a mating fashion, thus permitting the cap assembly 10/11/16 to be easily screwed onto and off of the reservoir 8. However, any other equivalent method can be used to sealably and removably attach the cap assembly 10/11/16 to the reservoir 8. When the apparatus 1 is in operational field use, it should be routinely maintained so that reservoir cavities 12 and 15 are refilled with liquid as required. When the cap assembly 10/11/16 is installed on the reservoir 8 it serves to seal the reservoir, preventing contamination and evaporation of the liquid contained therein, and also serves to provide a secondary seal for the measurement chamber 5.

Figure 5:
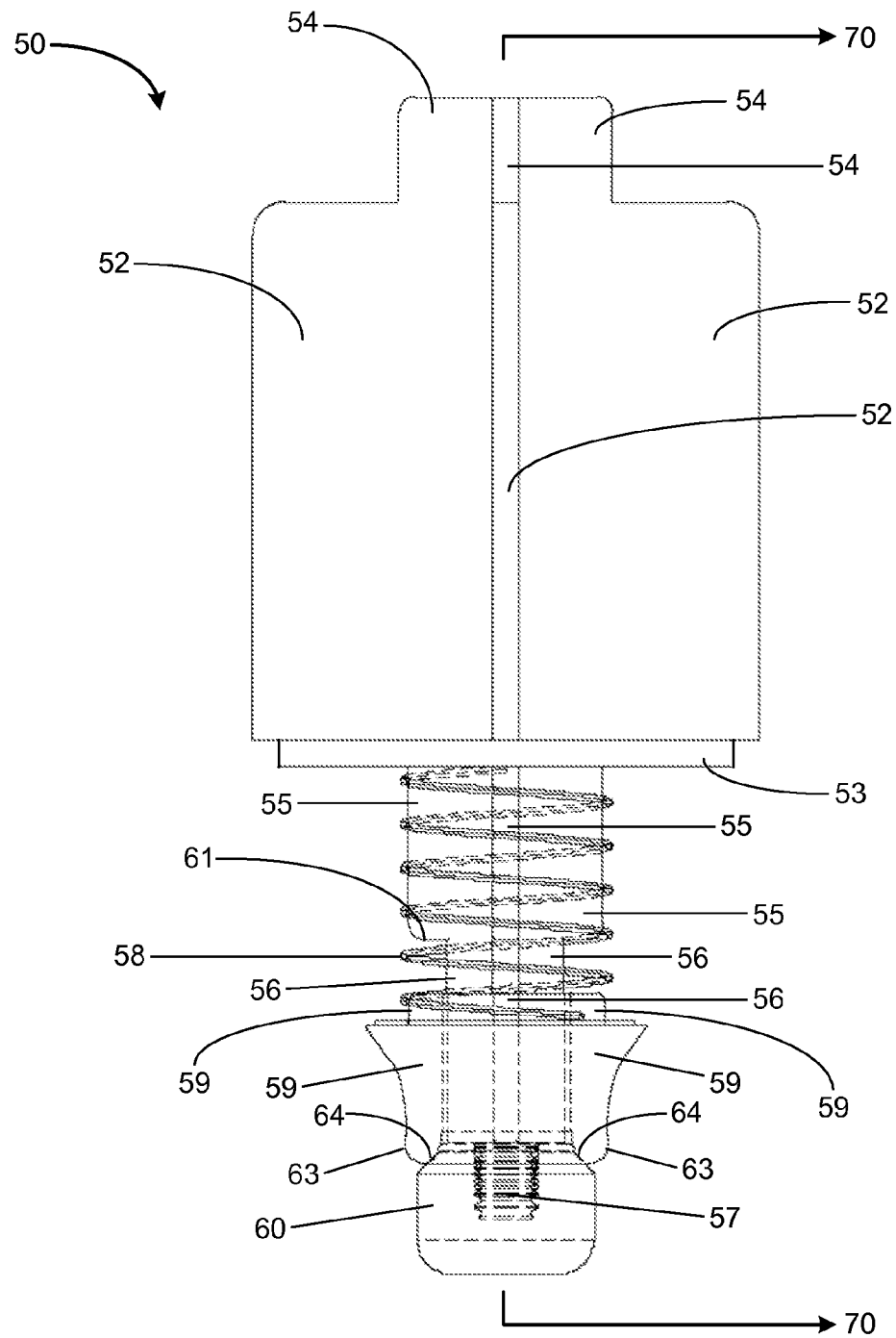
FIG. 5 shows an exemplary, stand-alone assembly, transparent longitudinal plan view of a spring-loaded, piston-type plunger mechanism according to the present invention with its valve in the normally closed position.
Figure 6:
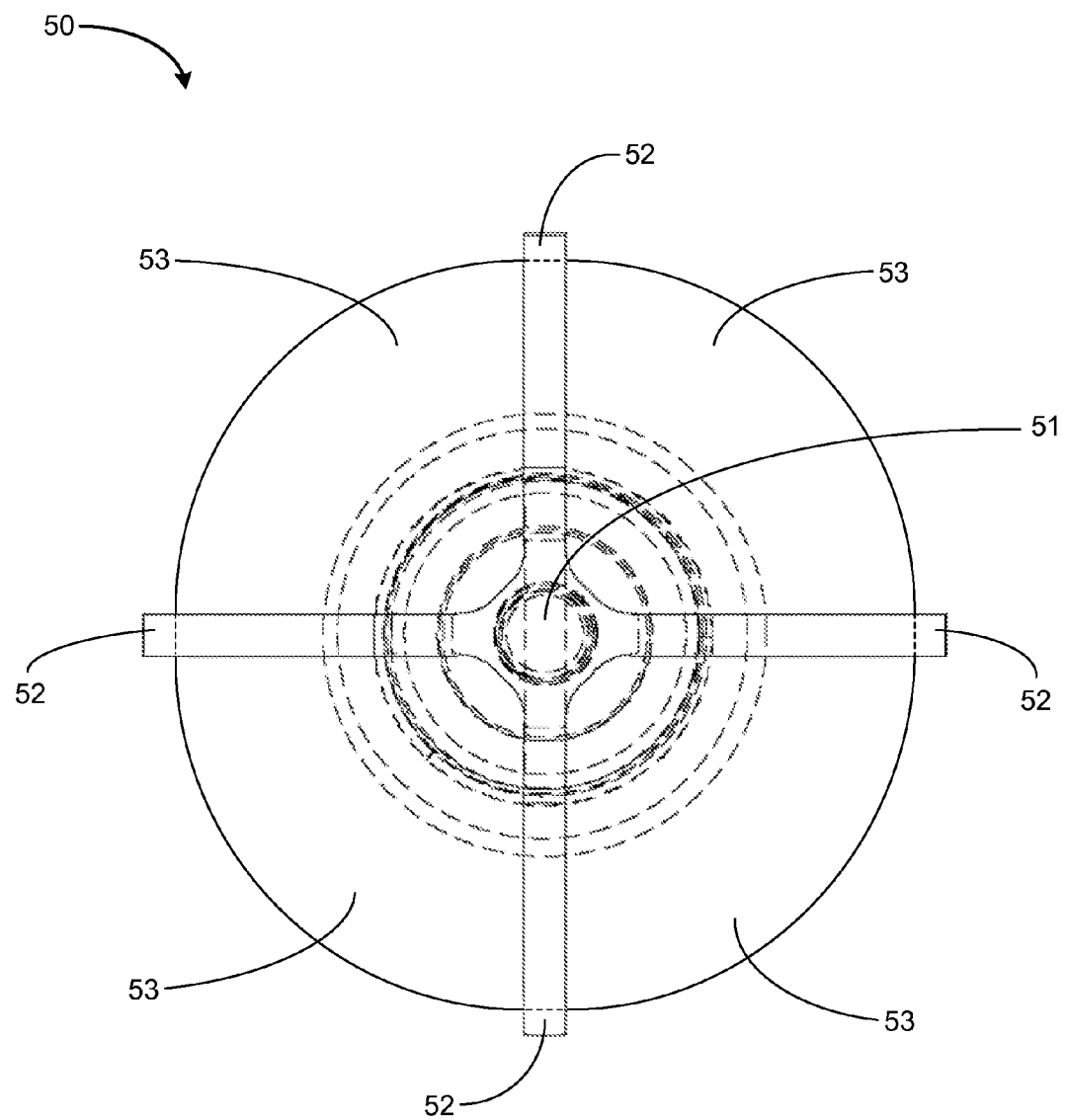
FIG. 6 shows an exemplary transparent top plan view of the plunger mechanism of FIG. 5.
Figure 7:
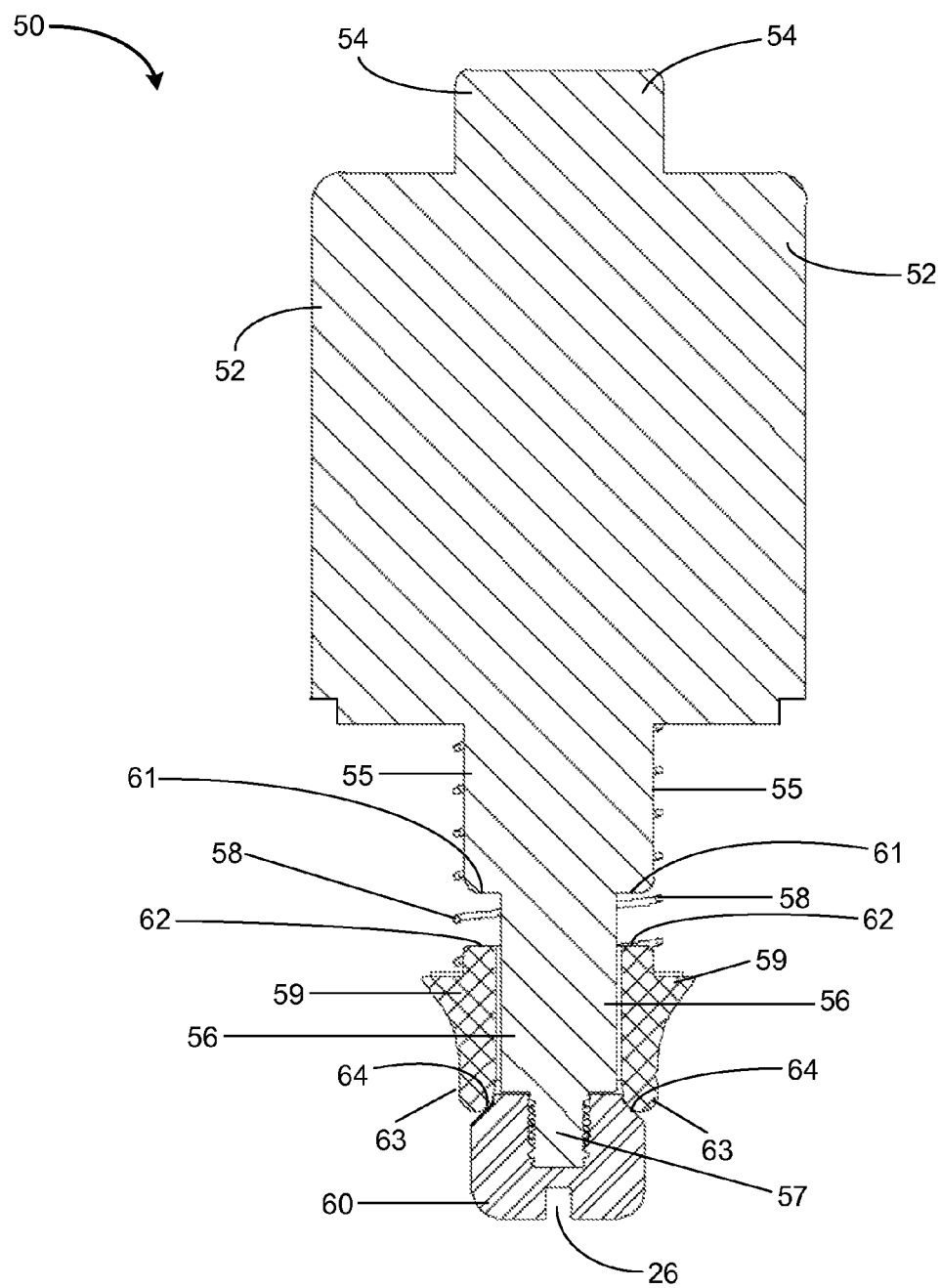
FIG. 7 shows an exemplary, stand-alone assembly, cross-sectional longitudinal view of the plunger mechanism of the present invention taken along line 70-70 of FIG. 5.

FIG. 5 shows an exemplary transparent longitudinal plan view of an embodiment of a spring-loaded, piston-type plunger mechanism 50, hereinafter also simply referred to as a plunger or plunger assembly, with its valve in the normally closed position. Note that FIG. 5 shows the plunger 50 as a stand-alone assembly (i.e., removed from the apparatus 1). FIG. 6 shows a corresponding exemplary transparent top plan view of the plunger 50 as a stand-alone assembly. FIG. 7 shows a corresponding exemplary cross-sectional longitudinal view of the plunger 50 as a stand-alone assembly taken along line 70-70 of FIG. 5. The plunger 50 includes the following parts. Referring to FIGS. 5-7, the main body of the plunger is rigidly comprised of a longitudinal stem 51. A plurality of longitudinal panels 52 are disposed onto the upper section of the stem 51. Each panel 52 extends radially outward from the stem 51 by the same distance. Four panels 52 are used in the embodiment of the plunger 50 shown in FIGS. 5-7. However, the particular number of panels can be varied based on a number of production variables such as the particular type of material and production method used to form the main body of the plunger. A horizontal disc 53 is disposed onto the midsection of the stem 51 such that the disc is oriented perpendicular to the stem and the stem passes through the center of the disc. Each panel 52 is also disposed perpendicularly onto the top horizontal surface of the disc 53. The radius of the longitudinal uppermost section of each panel 52 steps inward to form a smaller radius extension 54 to each panel. Each panel extension 54 extends radially outward from the stem 51 by the same distance. Longitudinal panels 55 are also disposed onto the lower section of the stem 51 underneath the disc 53. Each panel 55 extends radially outward from the stem 51 by the same distance. In the depicted embodiment, the number of panels 55 is the same as the number of panels 52/54 and each panel 55 is longitudinally aligned to be in the same plane as its counterpart panel 52/54. Each panel 55 is also disposed perpendicularly onto the bottom horizontal surface of the disc 53. The radius of each panel 55 is smaller than the radius of its counterpart panel 52. The radius of the longitudinally lowermost section of each panel 55 steps inward to form a smaller radius extension 56 to each panel. Each panel extension 56 extends radially outward from the stem 51 by the same distance.

Figure 14:
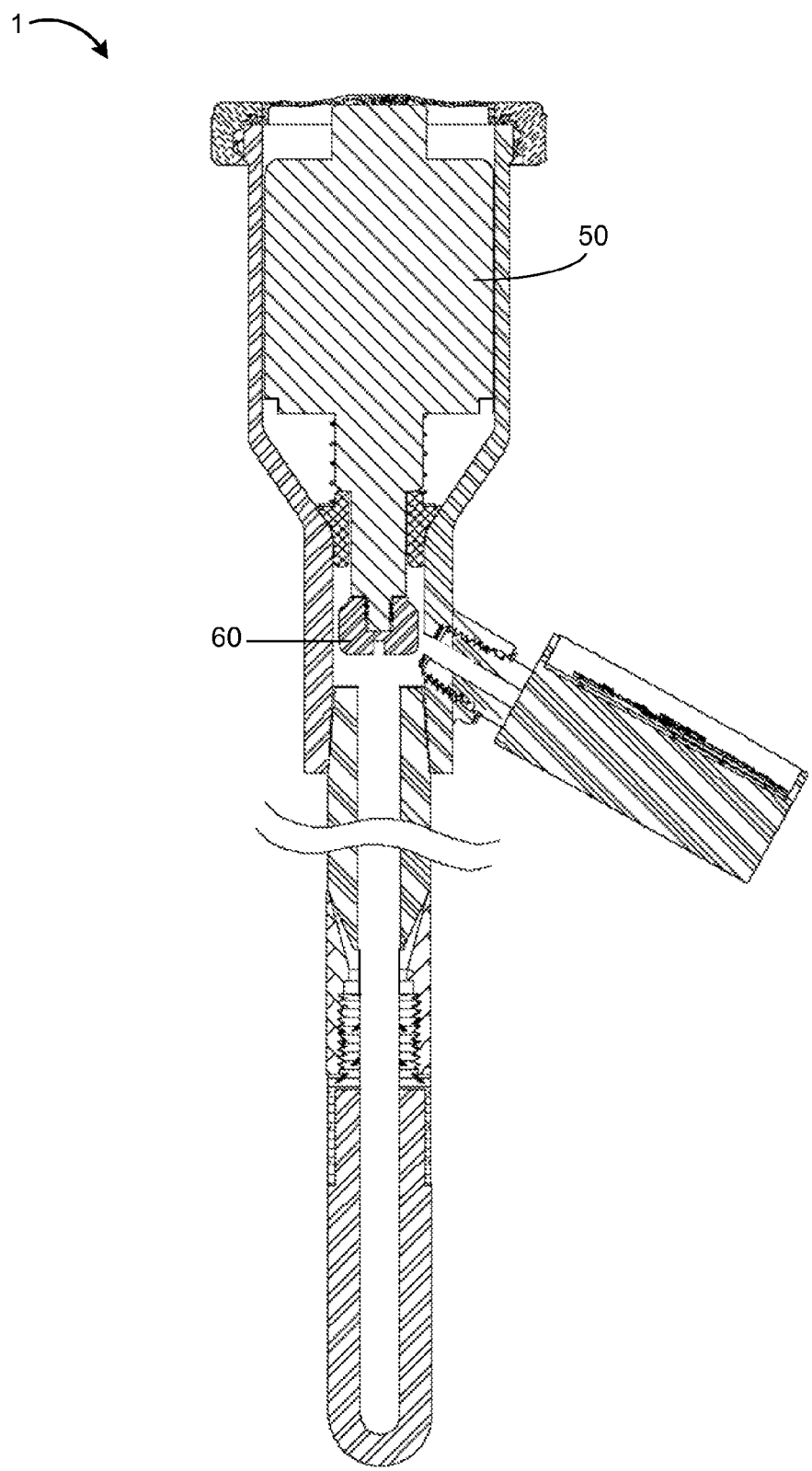
FIG. 14 shows an exemplary view of the tensiometer apparatus of FIG. 3 with its valve in a fully open position.

Referring again to FIGS. 5-7, a funnel-shaped cylindrical seal 59 is slidably fitted over the panel extensions 56. The diameter of the seal's 59 inner hollow cylinder is sized to allow the seal to freely slide up and down along the panel extensions 56. A post 57 is disposed onto the center of the bottom of the stem 51. A valve bulb 60 is attached to the bottom of the post 57. In the embodiment of the plunger 50 shown in FIGS. 5-7, the post 57 is threaded and the valve bulb 60 includes a matching threaded hole on its top end so that the valve bulb is removably attached to the post. However, other suitable methods of attaching the valve bulb 60 to the post 57 can also be used. In this embodiment, the bottom of the valve bulb 60 includes a slot 26 so that a tool such as a screwdriver (not shown) can be used to aid in attaching the valve bulb onto the post 57. However, slot 26 is optional and even if it is included, a tool is not required to attach the valve bulb 60 onto the post since other methods such as hand tightening can also be used. A compression spring 58 is slidably fitted over the panels 55/56 and is located between the disc 53 and the seal 59. The diameter of the spring 58 is sized to allow it to freely slide up and down along the panels 55/56. The size and length of the spring 58, in conjunction with the length of the post 57, are sized such that the spring pushes upwardly on the bottom horizontal surface of the disc 53 and pushes downwardly on the top of the seal 59 so that the seal 59 is downwardly urged against the valve bulb 60, resulting in what is herein termed a "normally closed" position of the valve. When the valve bulb 60 is forcibly pushed down away from the seal 59 (via an action which will be described in more detail hereinafter) the spring 58 is compressed, thus allowing the bulb to move away from the seal resulting in what is herein termed an "open" position of the valve, which is best shown in FIG. 14.

Referring again to FIGS. 1-4 and FIG. 5, the plunger 50 is slidably and removably fitted into reservoir cavities 12 and 15, and passageway 9. When the cap assembly 10/11/16 is removed from the reservoir 8 the plunger 50 can be slidably removed from reservoir cavities 12 and 15, and passageway 9. From a dimensional standpoint, the length of the upper section of the plunger's stem 51, and related lengths of its panels 52 and their extensions 54, are sized such that when the cap assembly 10/11/16 is installed onto the reservoir 8, a small gap 28 exists between the actuating button 16 and the top of the stem and panel extensions 54 such that the actuating button normally exerts no force onto the top of the stem and panel extensions. The size and length of the spring 58 is chosen so that the spring exerts a downward force onto the top of the seal 59 to keep it in place against the lower wall of the reservoir's funnel section 13, and exerts an upward force onto disc 53 so as to retain the top of the valve bulb 60 against the bottom of the seal, thus sealing the passageway 9 from the reservoir cavities 12 and 15 when the valve bulb is in its normally closed position.

Referring yet again to FIGS. 1-4 and FIG. 5, the shape of the seal 59 is designed to generally match the inner shape of the lower wall of the reservoir's funnel section 13. The outer surface of the bottom of the seal 63 contains a small bulge (not shown) such that when the plunger 50 is fitted into reservoir cavities 12 and 15, and passageway 9, the bulge contacts the bottom of the reservoir's funnel section 13, thus providing a good primary seal. The upper part of the seal 59, above the bulge, also contacts the lower part of the reservoir's funnel section 13, thus providing a secondary seal. As best shown in FIG. 7, the top of the valve bulb 60 tapers inward and the inner surface of the bottom of the seal 64 contains a small bulge (not shown) such that the bulge contacts the top of the valve bulb when the valve is in its normally closed position, thus providing a good seal, and thus allowing the aforementioned buildup of negative pressure and related vacuum in the chamber. The maximum diameter of the valve bulb 60 is sized such that ample space exists between the side surface of the valve bulb and the reservoir's lower tube 14 so that when the valve is in its open position, liquid can easily flow around the side surface of the valve bulb and down into the chamber 5. Furthermore, ample space exists around the side surface of the valve bulb 60 for the gauge 2 to accurately measure the negative pressure and related vacuum in the chamber 5 and passageway 9 for all possible positions of the valve bulb (i.e., the valve's normally closed position, completely open position and all positions in between). The width of the panel extensions 54 is sized such that the diameter of the radial area defined by their edges approximately matches the diameter of the inside surface of the actuating button 16. The width of the panels 52 is sized such that the diameter of the radial area defined by their edges is close to but slightly less than the diameter of cavity 12 defined by the reservoir wall 8, thus allowing the plunger assembly 50 to snugly but slidably fit within the reservoir wall without any possibility of the plunger assembly binding against the wall as the valve bulb 60 is moved between its normally closed and open positions. The diameter of the disc 53 is sized such that it is slightly less than the diameter of the radial area defined by the width of the panels 52, thus allowing liquid to flow in a constricted fashion from cavity 12 into the lower cavity 15.

Referring yet again to FIGS. 1-4 and FIG. 5, when the plunger 50 is slidably and removably fitted into reservoir cavities 12 and 15, and passageway 9, and the optional cap assembly 10/11/16 is installed onto the reservoir 8, the plunger serves a number of different functions including but not limited to the following. As described heretofore, in its nominal (i.e., not depressed) state the valve bulb 60 is forcibly retained against the seal 59 in the valve's normally closed position by spring 58, serving to seal the passageway 9 from reservoir cavities 12 and 15, and thus sealing the passageway 9 and measurement chamber 5. Since the passageway 9 operates as an extension of the chamber 5, the sealed cavity formed by the passageway and chamber will hereinafter generally be simply referred to as the chamber 5. As will now be described, the plunger 50 basically operates in three steps to refill the liquid in the chamber 5 and remove the air which has accumulated therein. When an operator depresses the actuating button 16 by applying a downward force to it, the flexible membrane 11 flexes downward and the button comes in contact with the top of the plunger's stem 51 and applies a downward force to the plunger's stem, causing the spring 58 to compress and the valve bulb 60 to move away from the seal 59 into the valve's open position. With the valve bulb 60 in its open position the passageway 9 is opened to the reservoir cavities 12 and 15 above, thus allowing low pressure air which has accumulated in the chamber 5 over time to escape into the cavities, and allowing liquid in the cavities to flow through the valve opening into the chamber 5 to replace the air which escaped. As the plunger's stem 51 continues to move downward, the valve bulb 60 is further opened and the flow of liquid into the chamber 5 is accelerated by the plunger's disc 53, whose relatively large surface area moves downward in conjunction with the stem and valve bulb. This downward movement of the disc 53 serves to forcibly pump liquid inside cavity 15 downward through the valve opening and into the chamber 5 in what is herein termed "jet-action" (i.e., the disc generates a turbulent flow of liquid into the chamber). The turbulent flow of liquid into the chamber 5 serves to purge practically all of the air remaining in the chamber, including but not limited to air bubbles on the chamber wall, by forcibly sweeping the bubbles away. The plunger's rigid body (comprising the stem 51, disc 53, panels 55 underneath the disc, valve bulb 60, and other parts discussed heretofore) continues to move downward until the bottommost surfaces 61 on the panels 55 contact the uppermost surface 62 on the seal 59, at which point the plunger's rigid body stops moving downward and the valve bulb has reached it fully open position. This fully open position of the valve bulb 60 is best shown in FIG. 14. Finally, when the operator releases the button 16, the downward force on the plunger's 50 stem 51 is released, allowing the spring 58 to decompress and forcibly push the plunger's rigid body upward in a return stroke until the valve again reaches its normally closed position and there is again a small gap between the button and the top of the plunger's stem. The return stroke of the disc 53 creates a partial vacuum and related negative pressure in the chamber 5 which causes air bubbles remaining in the chamber to expand, thus further purging the chamber of air remaining therein by causing at least some of the bubbles remaining on the chamber wall to break loose from the wall and be drawn into reservoir cavities 12 and 15. When the plunger's rigid body completes its return stroke and the valve bulb 60 reaches its normally closed position, the passageway 9 from reservoir cavities 12 and 15 to the chamber 5 is closed and the chamber is re-sealed without applying positive pressure to the chamber. Air removed from the chamber 5 collects at the top of the reservoir 8. The particular difference between the diameter of the disc 53 and the diameter of cavity 12 is selected to provide a desired pumping force of liquid into the chamber 5 during the downward movement of the disc and a desired level of partial vacuum and related negative pressure in the chamber during the return stroke of the disc.

Referring yet again to FIGS. 1-4, the gauge 2 is sealably attached to the lower tube 14 of the reservoir, beneath the normally closed position of the valve bulb 60 and above the top of the tube 4. A tube 24 on the gauge 2 forms a passageway 7 between the gauge and reservoir passageway 9. The passageway 7 allows the gauge 2 to measure the current level of negative pressure and related vacuum in the chamber 5, and hence the moisture content of the soil. As previously noted, ample space exists around the side surface of the valve bulb 60 for the gauge 2 to accurately measure the negative pressure and related vacuum in the chamber 5 for all possible positions of the valve. In order to facilitate easy servicing and replacement of the gauge 2, it is preferable that the method of sealably attaching the gauge to the reservoir tube 14 permit the gauge to be easily removed from, and installed back onto, the reservoir tube. In the embodiment of the present invention shown in FIGS. 1-4, this is accomplished as follows. The gauge tube 24 is externally threaded and a protruding tube 25 on the reservoir tube 14 includes a mating internally threaded passageway into which the gauge's externally threaded tube is installed. An O-ring 21 is fitted onto the gauge tube 24 to further enhance the seal. The passageway 7 is directed at a downward angle (i.e., towards the porous tip 3) so that liquid will remain in the passageway and the gauge 2 will be kept in contact with the liquid in the event that the liquid level in the chamber 5 falls below the passageway. Any type of conventional vacuum gauge can be used. A dial-type gauge is shown in the depicted embodiments, which includes a dial 27 for indicating the moisture content of the soil to an observer.

Figure 8:
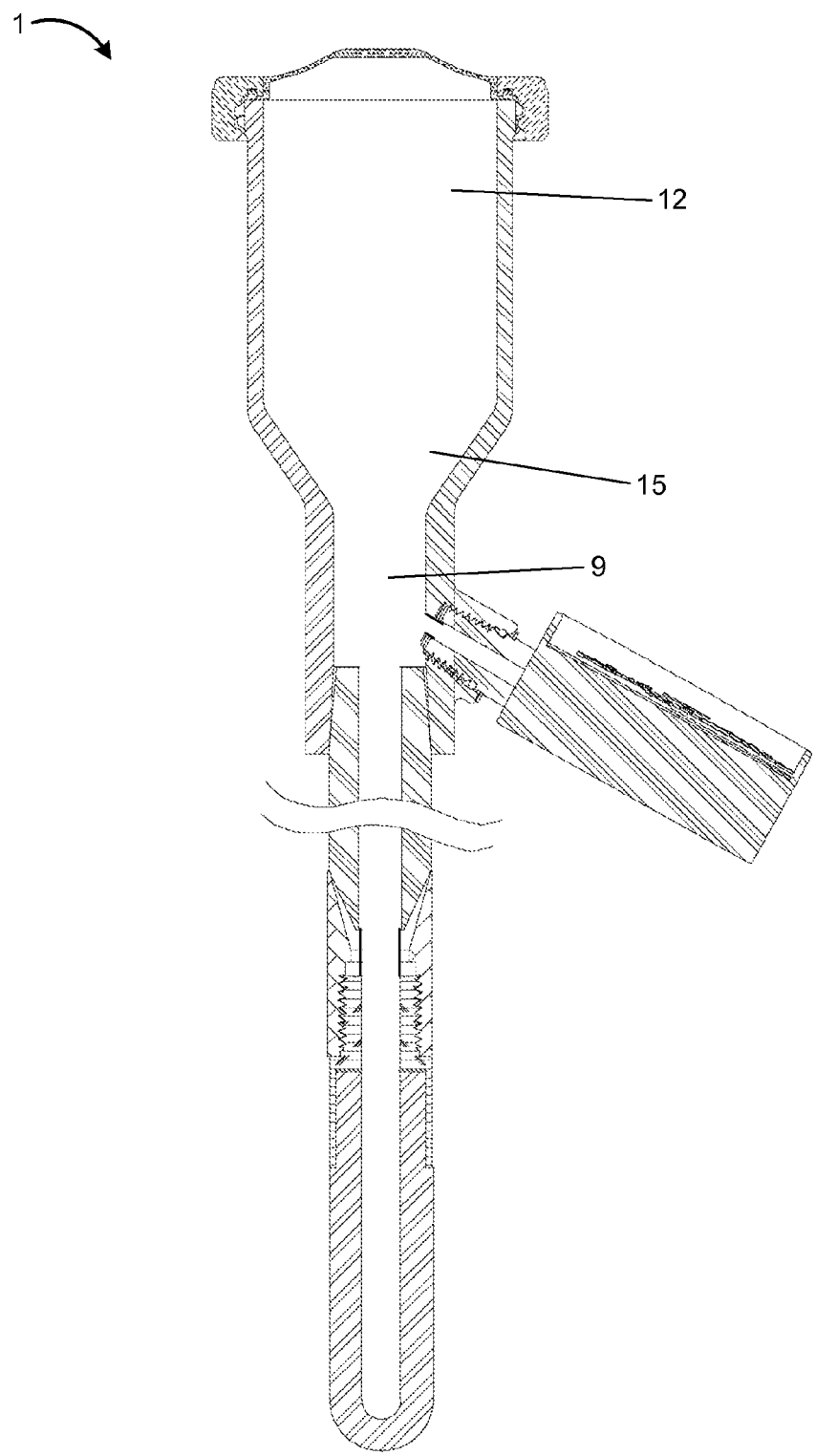
FIG. 8 shows an exemplary cross-sectional longitudinal view of the apparatus of FIG. 3 with the plunger mechanism of FIGS. 5-7 removed.

The following additional FIGs. are presented as a further aid to understanding the present invention. FIG. 8 shows the apparatus 1 of FIG. 3 with the plunger assembly 50 removed. This clearly depicts the contiguous nature of the upper cavity 12, lower cavity 15 and passageway 9 comprised within the reservoir 8/13/14.

Figure 9:
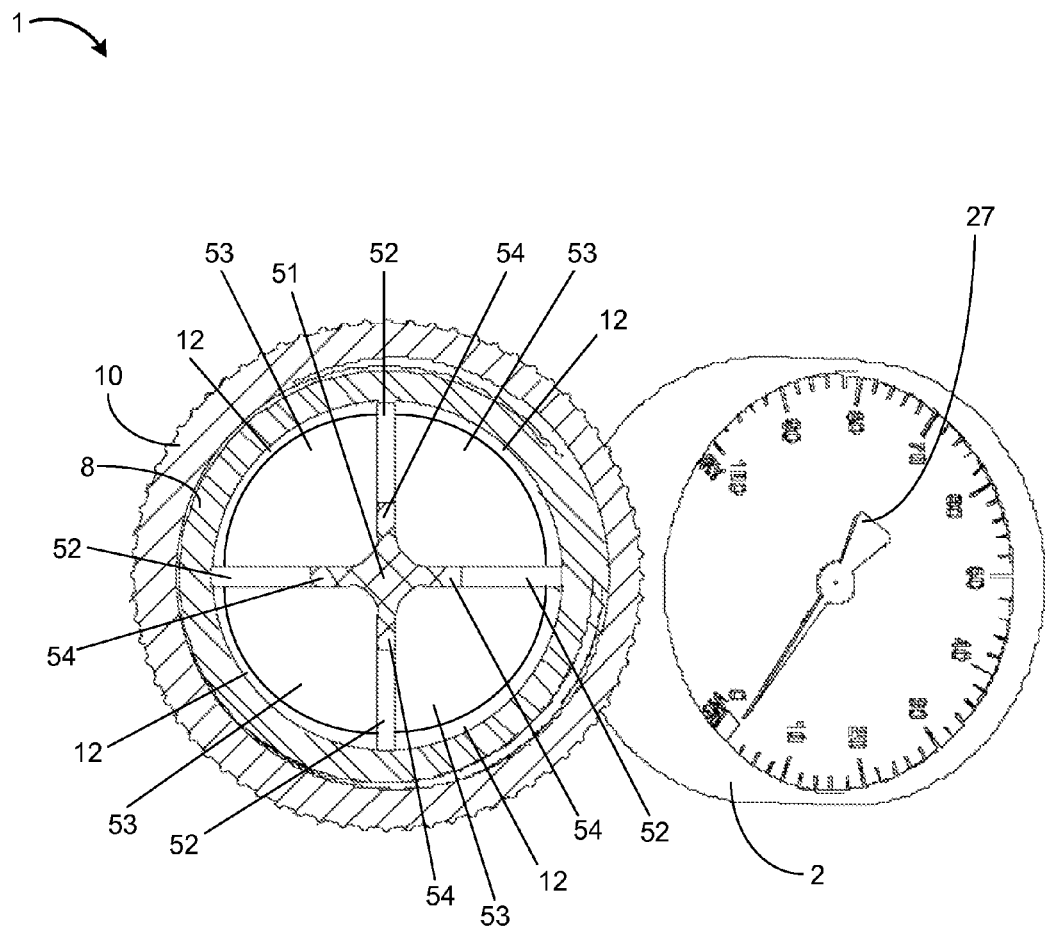
FIG. 9 shows an exemplary cross-sectional top view of the tensiometer apparatus of the present invention taken along line 90-90 of FIG. 1.

FIG. 9 shows an exemplary cross-sectional top view of the apparatus 1 taken along line 90-90 of FIG. 1. More particularly, FIG. 9 depicts the cap ring 10, reservoir wall 8, plunger disc 53, reservoir upper cavity 12, plunger stem 51, plunger panels 54, plunger panels 52, and a top perspective view of the gauge 2.

Figure 10:
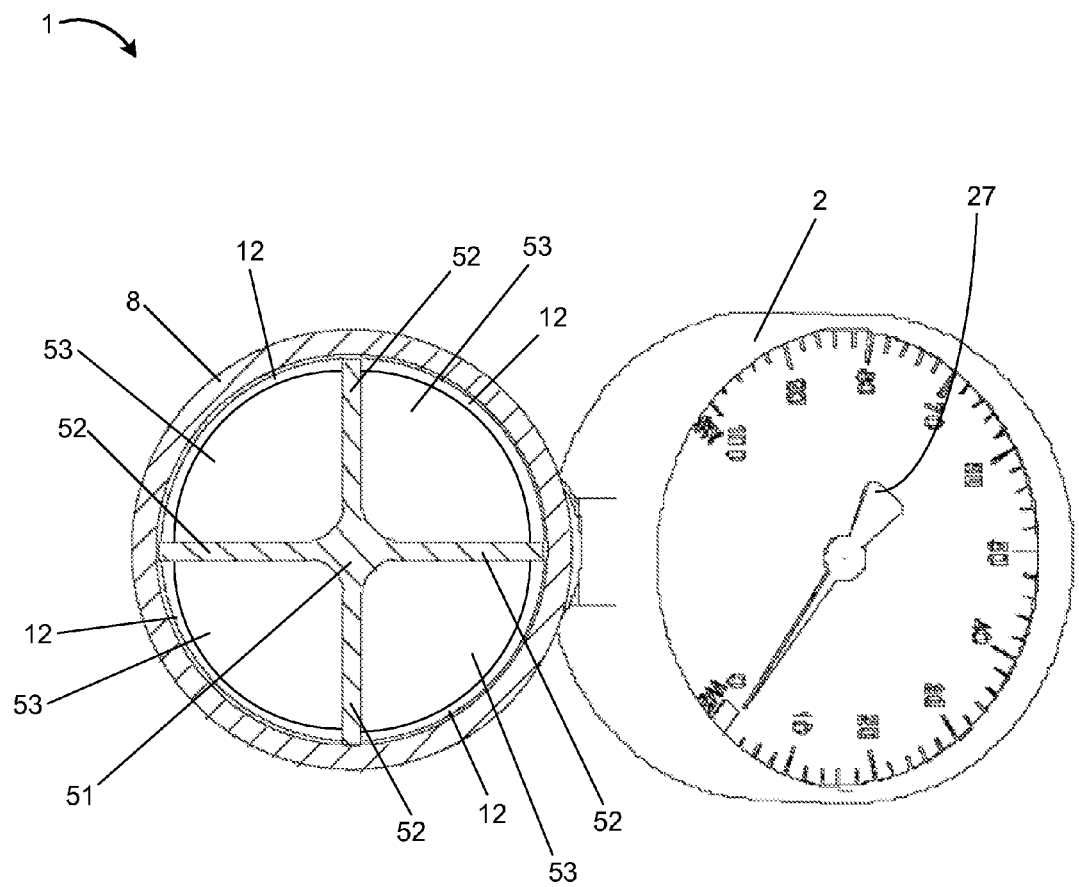
FIG. 10 shows an exemplary cross-sectional top view of the tensiometer apparatus of the present invention taken along line 100-100 of FIG. 1.

FIG. 10 shows an exemplary cross-sectional top view of the apparatus 1 taken along line 100-100 of FIG. 1. More particularly, FIG. 10 depicts the reservoir wall 8, plunger disc 53, reservoir upper cavity 12, plunger stem 51, plunger panels 52, and a top perspective view of the gauge 2.

Figure 11:
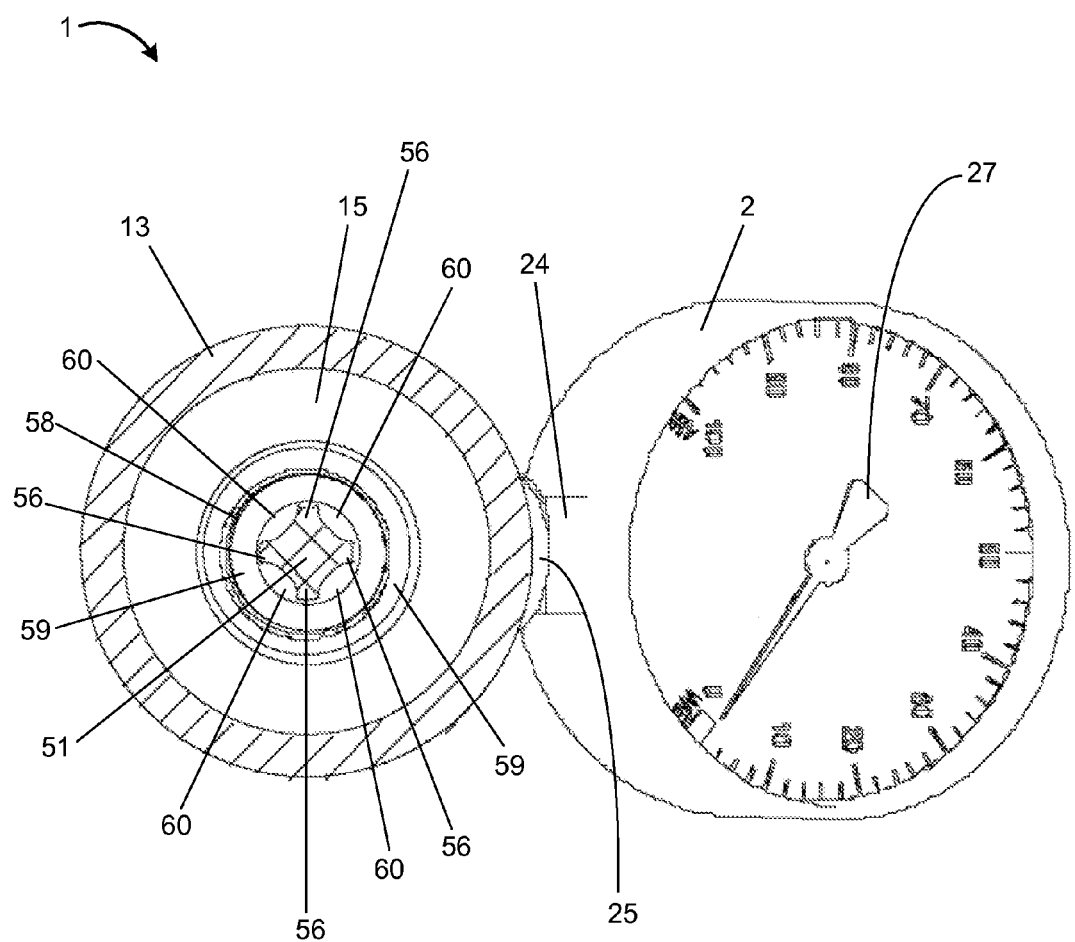
FIG. 11 shows an exemplary cross-sectional top view of the tensiometer apparatus of the present invention taken along line 110-110 of FIG. 1.

FIG. 11 shows an exemplary cross-sectional top view of the apparatus 1 taken along line 110-110 of FIG. 1. More particularly, FIG. 11 depicts the reservoir wall 13, reservoir lower cavity 15, plunger stem 51, plunger panels 56, plunger valve bulb 60, plunger seal 59, plunger spring 58, and a top perspective view of the reservoir projecting tube 25, gauge 2, and gauge tube 24.

Figure 12:
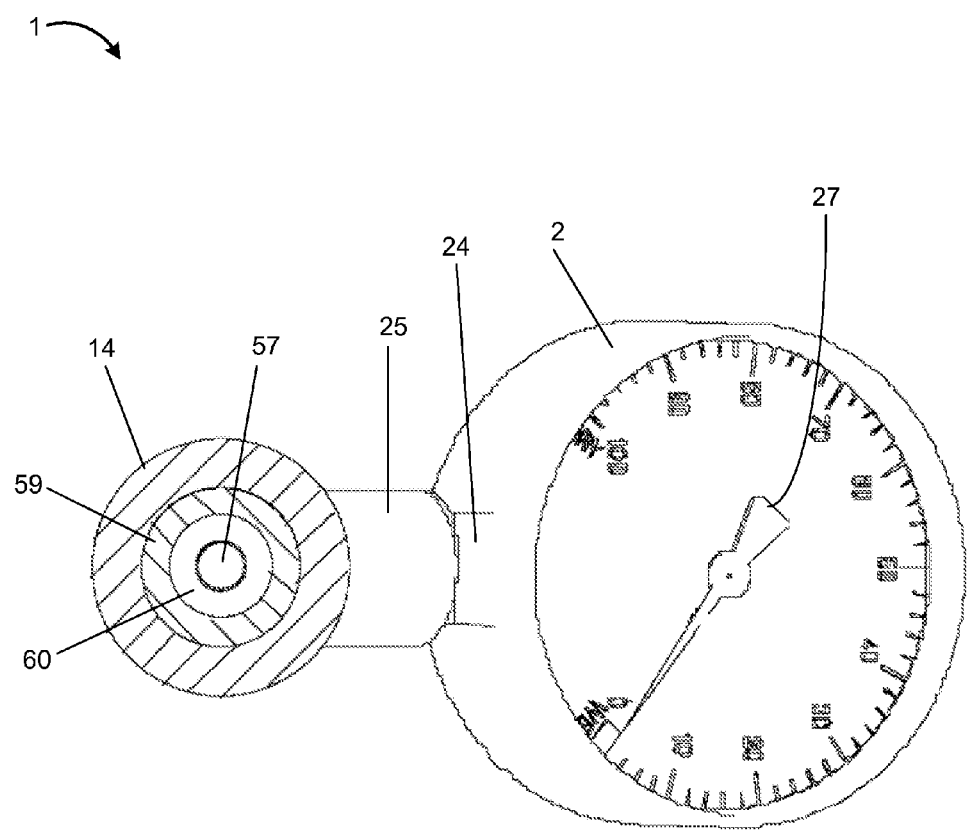
FIG. 12 shows an exemplary cross-sectional top view of the tensiometer apparatus of the present invention taken along line 120-120 of FIG. 1.

FIG. 12 shows an exemplary cross-sectional top view of the apparatus 1 taken along line 120-120 of FIG. 1. More particularly, FIG. 12 depicts the reservoir tube 14, plunger seal 59, plunger valve bulb 60, plunger post 57, and a top perspective view of the reservoir projecting tube 25, gauge 2, and gauge tube 24.

FIG. 14, as discussed heretofore, shows an exemplary view of the apparatus 1 with the plunger 50 and its valve bulb 60 in their fully depressed state, and the valve correspondingly in its fully open position.

The following are examples of the types of materials and methods that can be used to make the apparatus 1 of the present invention. Particular material and production method requirements are noted herein where applicable. However, it should be appreciated that other types of equivalent materials and production methods can be substituted without departing from the spirit and scope of the present invention. The porous tip 3 should be made from any of a wide variety of rigid porous materials, including but not limited to ceramics. This material should be rigid so as not to deform or break when pushed into soil or other like medium (not shown). This material should also have a "bubbling pressure" (i.e., the pressure below which air will not pass through wetted pours of the material) that is greater than normal atmospheric pressure in order to inhibit bubbles of air from entering the measurement chamber 5 through the tip 3. The tube 4, reservoir 8/13/14, cap ring 10, and rigid parts of the plunger's body 51/52/53/54/55/56/57/60 should be made of a rigid material such as plastic, which can relatively inexpensively be formed using conventional injection molding methods. This material can be transparent so that the liquid level in the apparatus 1 is easily observed. The plunger seal 59 and cap flexible membrane 11 should be made from a flexible but relatively stiff material such as rubber or another suitable material, which can relatively inexpensively be formed using conventional injection molding methods. Since the apparatus 1 will be subjected to long periods of moisture when in operational field use (such as liquid held inside the apparatus, moisture in the soil or other like medium into which the apparatus is inserted, and rain and other forms of moisture in the field in which the apparatus operates), all the materials used to make the apparatus should be non-corrosive.

Figure 13A:
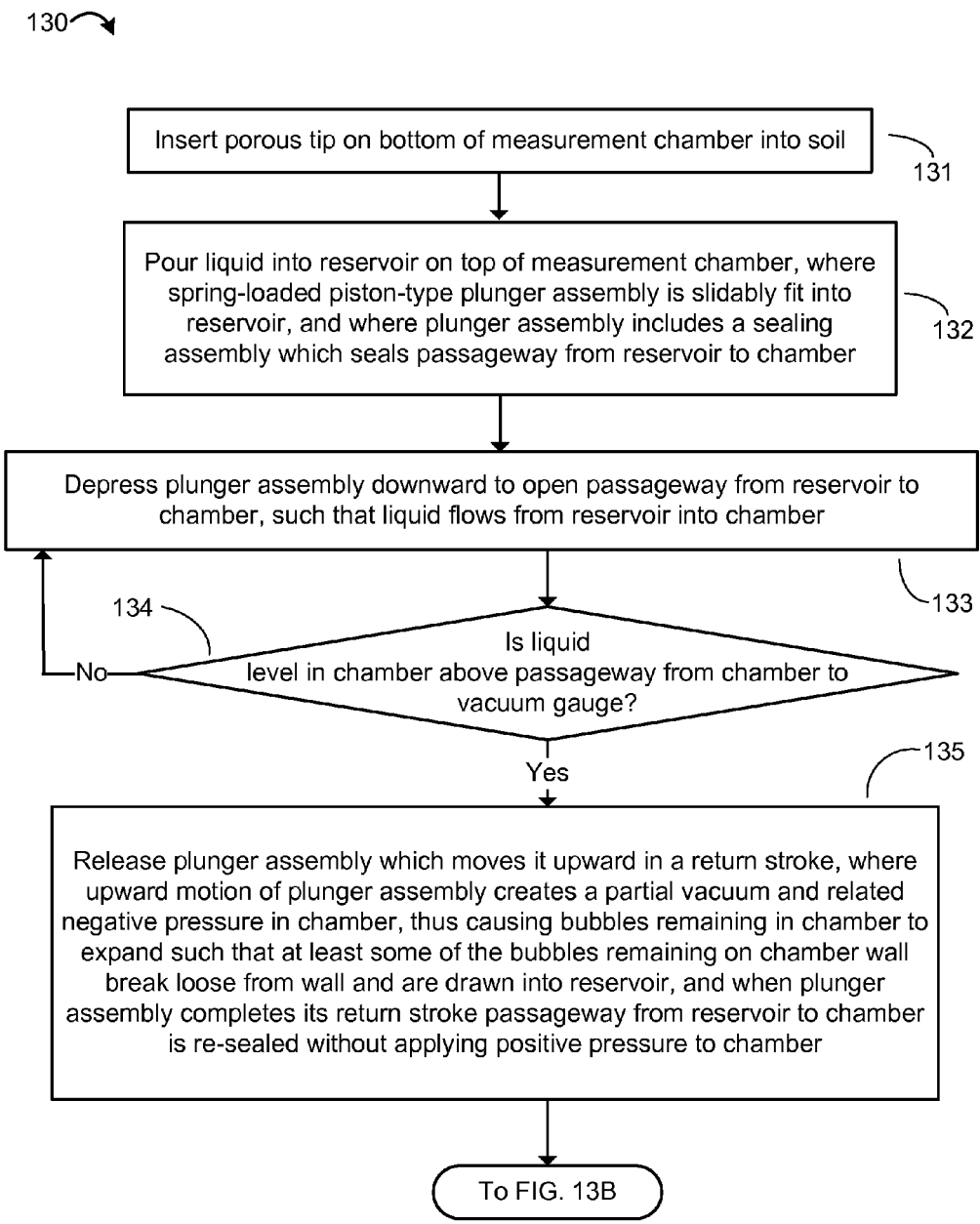
FIGS. 13A and 13B show an exemplary flow diagram of a soil moisture content measurement process according to the present invention.
Figure 13B:
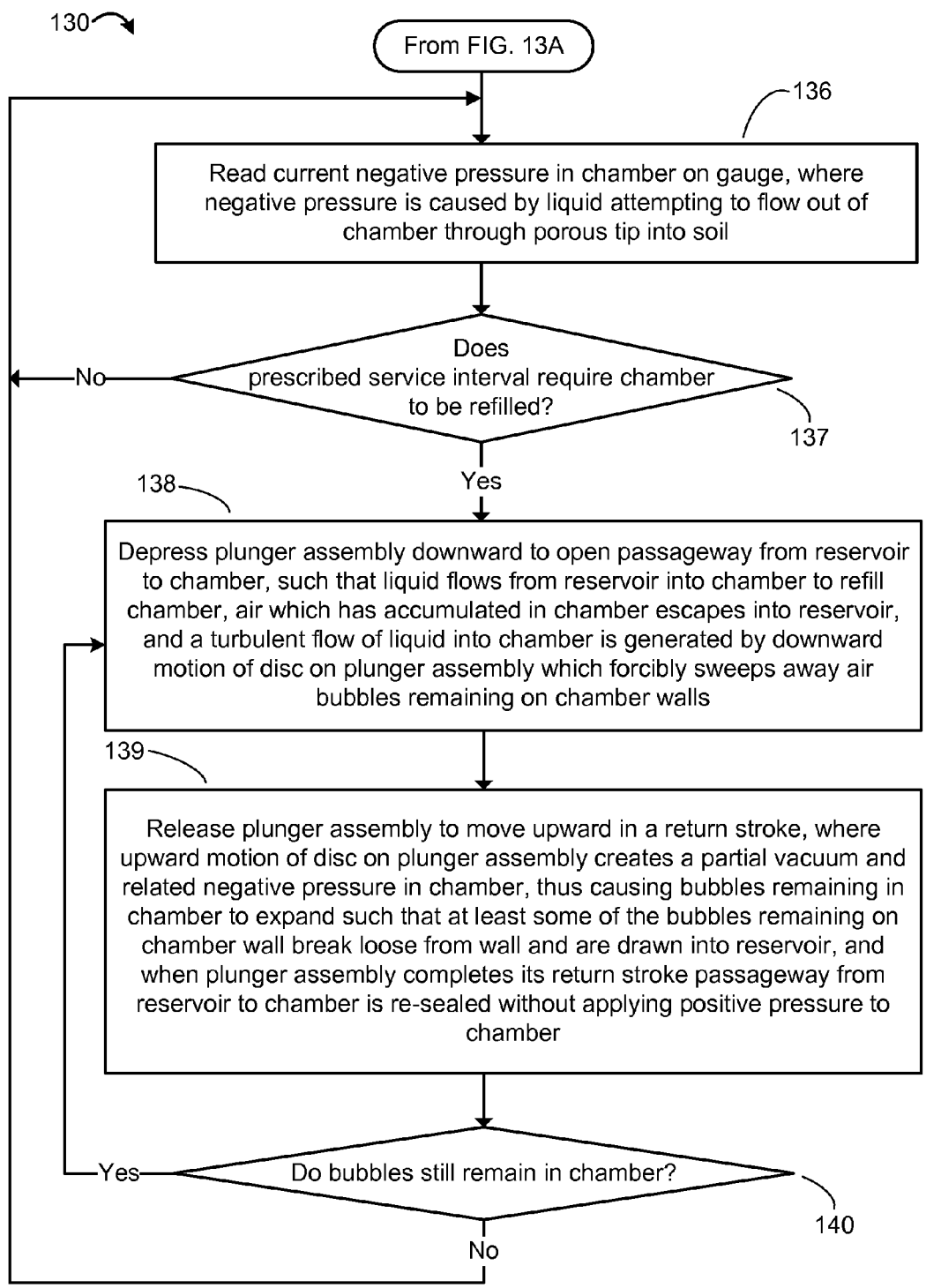

FIGS. 13A and 13B show an exemplary flow diagram of the present process 130 for measuring the moisture content of soil and other like medium using a tensiometer. The process starts by inserting a porous tip located on the bottom of a measurement chamber into the soil 131. Liquid is then poured into a reservoir located on the top of the measurement chamber, where a spring-loaded, piston-type plunger assembly is slidably fit into the reservoir, and where the plunger assembly includes a sealing assembly which seals a passageway from the reservoir to the chamber 132. The plunger assembly is then depressed downward to open the passageway from the reservoir to the measurement chamber, such that liquid flows from the reservoir into the chamber 133. Once the liquid level in the measurement chamber rises above a passageway from the chamber to a vacuum gauge 134, the plunger assembly is then released which moves it upward in a return stroke, where the upward motion of the plunger assembly creates a partial vacuum and related negative pressure in the chamber, thus causing bubbles remaining in the chamber to expand, such that at least some of the bubbles remaining on the chamber wall break loose from the wall and are drawn into the reservoir, and when the plunger assembly completes its return stroke the passageway from the reservoir to the chamber is re-sealed without applying a positive pressure to the chamber 135. The current level of negative pressure in the measurement chamber can then be periodically read on the gauge, where the negative pressure is primarily caused by the liquid attempting to flow out of the chamber, through the porous tip, into the soil 136. On a routine basis as required based on a prescribed measurement chamber refill service interval 137, the plunger assembly is depressed downward to open the passageway from the reservoir to the chamber, such that liquid flows from the reservoir into the chamber to refill the chamber, air which has accumulated in the chamber escapes into the reservoir, and a turbulent flow of liquid into the chamber is generated by the downward motion of a disc on the plunger assembly which forcibly sweeps away bubbles remaining on the chamber walls 138. The plunger assembly is then released, allowing it to move upward in a return stroke where the upward motion of the disc on the plunger assembly creates a partial vacuum and related negative pressure in the measurement chamber, thus causing bubbles remaining in the chamber to expand, such that at least some of the bubbles remaining on the chamber wall break loose from the wall and are drawn into the reservoir, and when the plunger assembly completes its return stroke the passageway from the reservoir to the chamber is re-sealed without applying a positive pressure to the chamber 139. If any bubbles still remain in the measurement chamber 140, process steps 138 and 139 may be repeated until the remaining bubbles are purged from the chamber.

While the present invention has been described in detail by specific reference to preferred embodiments thereof, it is understood that variations and modifications thereof may be made without departing from the true spirit and scope of the present invention. By way of example, either in place of or in addition to the diameter of the disc 53 being slightly less than the diameter of the radial area defined by the width of the panels 52, perforations (not shown) can be added to the disc. The particular number of perforations and the size of each perforation would be selected, in conjunction with the particular size of the disc 53, to provide a desired pumping force of liquid into the chamber 5 during the downward movement of the disc and a desired level of partial vacuum and related negative pressure in the chamber during the return stroke of the disc. By way of further example, the number of panels 52/54/55/56 employed on the plunger assembly 50 can be varied based on various production variables such as the particular type of material and production method used to form the plunger. By way of yet further example, although a coupling adapter 18 is used to attach the measurement tube 4 to the porous tip 3, any other equivalent method of sealably and removably attaching the tube to the tip can be employed. The porous tip 3 can also be sealably and non-removably attached to the measurement tube 4 via a range of different methods including gluing. By way of yet further example, although an O-ring 21 is used to attach the gauge 2 to the apparatus 1, any other equivalent method of sealably and removably attaching the gauge to the apparatus can be employed. The gauge 2 can also be sealably and non-removably attached to the apparatus 1 via a range of different methods including gluing. By way of yet further example, depending on the type of material used for the plunger seal 59, a washer (not shown) can be installed between the plunger spring 58 and seal to prevent the possibility of the spring damaging the seal over time. By way of yet further example, although the plunger assembly 50 is described and illustrated herein as being operated manually via depressing and releasing the actuating button 16, the apparatus 1 can be easily adapted such that the plunger 50 is automatically operated by a remotely energized solenoid (not shown). If the solenoid is then remotely connected to a central control station (not shown), the required routine service operation of refilling the chamber 5 with liquid can then be performed remotely on a large number of apparatus 1 without requiring manual interaction with each individual apparatus. By way of yet further example, in the process 130 for measuring the moisture content of soil and other like medium using a tensiometer, the measurement chamber 5 can optionally be initially filled with liquid by pouring the liquid directly into the chamber before the plunger assembly 50 is slidably fitted into the reservoir 8/13/14. Once the liquid level in the chamber 5 is above the passageway 7 from the chamber to the gauge, the plunger assembly 50 can then be slidably fitted into the reservoir 8/13/14 to seal the passageway from the reservoir to the chamber, and then liquid can be poured into the reservoir in order to fill it with the liquid. This alternative method of initially filling the measurement chamber 5 with liquid may be useful if the plunger assembly 50 is ever removed from the reservoir 8/13/14 for servicing as discussed below. By way of final example, it should be noted that the cap assembly 10/11/16 is an optional feature of the apparatus 1. In the case where no cap assembly 10/11/16 is installed on the apparatus 1, then the downward force would be applied directly to the top of the plunger assembly's 50 stem 51 and panels 54.

With particular regard to the serviceability and maintenance features of the apparatus 1 of the present invention, as has been discussed heretofore, the cap assembly 10/11/16 is easily removed from the apparatus and the flexible membrane 11 is easily removed from the cap assembly, allowing the membrane to be serviced or replaced in the event that it becomes worn or damaged. The plunger assembly 50 is easily removed from the reservoir 8/13/14, allowing it to be serviced or replaced in the event that it becomes worn or damaged. The spring 58, seal 59 and valve bulb 60 are easily removed from the plunger assembly 50, allowing them to be serviced or replaced in the event that they become worn or damaged. The gauge 2 is easily removed from the reservoir tube 25, and the porous tip 3 is easily removed from the coupling adapter 18 on the measurement tube 4, allowing them to also be serviced or replaced in the event that they become worn or damaged. As discussed below, none of the aforementioned service and maintenance operations requires the use of tools.

As is apparent from the foregoing, the present invention addresses the disadvantages of conventional tensiometers and in general, significantly advances the state of the art of tensiometers. By way of example but not limitation, the following are some advantages of the tensiometer apparatus 1 and process 130 of the present invention. The required operation of routinely refilling the measurement chamber 5 with liquid is much easier and faster than with conventional tensiometers since the operator simply has to depress and release the plunger assembly 50 contained within the apparatus 1. There is no need to manually remove a seal from the apparatus 1, or to manually pour liquid into the apparatus, or to manually re-install the seal onto the apparatus each time the operator refills the chamber 5 with liquid, as is the case with most conventional tensiometers. The action of depressing and releasing the plunger assembly 50 to refill the chamber 5 results in the chamber's seal being removed for only a minimal period of time compared to conventional tensiometers, so that much less unwanted liquid flows out of the chamber through the porous tip 3 into the surrounding soil during the refill operation. The amount of unwanted liquid that flows into the soil during the chamber 5 refill operation is further reduced by the fact that the reservoir 8/13/14 which supplies the liquid is sealed by the cap assembly 10/11/16, and since the cap assembly does not have to be removed to perform the chamber refill operation, the reservoir seal is maintained during the chamber refill operation. As such, besides minimizing the duration of time during which the chamber's 5 seal is removed, the size of the pressure differential that is applied to the chamber is also minimized, thus further minimizing the amount of unwanted liquid that flows out of the chamber into the surrounding soil. No positive pressure is applied to the chamber 5 when it is re-sealed, thus even further minimizing the amount of unwanted liquid that flows out of the chamber into the surrounding soil. The turbulent flow of liquid into the chamber 5 created by the downward movement of the disc 53 on the plunger assembly 50 during the chamber refill operation, along with the partial vacuum and related negative pressure created in the chamber by the return stroke of the disc, results in a more effective and complete removal of the air which has accumulated and is entrapped in the chamber, even for a chamber with a relatively small diameter. The chamber 5 refill operation is performed without applying torque to the apparatus 1, thus eliminating any degradation in moisture measurement accuracy due to disturbing the porous tip's 3 liquid contact with the soil, which occurs in most conventional tensiometers.

By way of further example but not limitation, the following are some additional advantages of the tensiometer apparatus 1 and process 130 of the present invention. The overall structure and design of the apparatus 1 is greatly simplified and has fewer parts in comparison to conventional tensiometers. Assembly of the apparatus 1, along with removal and replacement of its parts as required for maintenance and service, is conveniently and relatively inexpensively accomplished without the use of tools. The end result of the various aforementioned advantages is a tensiometer which is easier to use, is easier and lower cost to manufacture and maintain, and has improved measurement sensitivity and accuracy, higher reliability, and a longer operating lifetime than conventional tensiometers.

It should be noted that any or all of the aforementioned alternate embodiments may be used in any combination desired to form additional hybrid embodiments. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Wherefore, what is claimed is:

1. A tensiometer apparatus for measuring the moisture content of soil and other like medium, comprising:
    an elongated measurement tube whose interior provides an elongated sealable measurement chamber which is normally filled with liquid;
    a porous tip which is sealably attached to the bottom end of the tube, wherein the tip is inserted into the soil and a passageway exists between the chamber and tip which allows liquid in the chamber to flow into the tip;
    a reservoir whose bottom end is sealably attached to the top end of the tube, wherein a passageway exists between the reservoir and chamber, and the reservoir is normally filled with liquid;
    a piston-type plunger assembly which is slidably fitted inside the reservoir and the passageway between the reservoir and chamber, wherein the plunger assembly comprises,
        a valve assembly located on the bottom end of the plunger assembly, wherein the valve assembly is normally closed such that the passageway between the reservoir and chamber is normally closed, and wherein whenever a downward force is applied to the plunger assembly it moves downward towards the chamber causing the valve assembly to open such that the passageway between the reservoir and chamber is opened so that liquid in the reservoir is allowed to flow into the chamber to refill the chamber and air which has accumulated in the chamber is allowed to escape into the reservoir,
        a pump assembly which, whenever the downward force is applied to the plunger assembly, forcibly pumps liquid from the reservoir, through the opened passageway between the reservoir and chamber, into the chamber, causing a turbulent flow of liquid into the chamber which purges air from the chamber by forcibly sweeping air bubbles from its wall, wherein the pump assembly comprises a horizontal planar member, and wherein,
        the planar member is oriented perpendicular to the direction of motion of the plunger assembly,
        the planar member has the same shape as the horizontal cross-sectional shape of the interior of the upper section of the reservoir, and is sized such that it extends close to but slightly short of the interior wall of the upper section of the reservoir so that liquid in the reservoir flows between the edges of the planar member and the reservoir walls,
        when the downward force is applied to the plunger assembly, the planar member moves downward and pumps liquid downward from the reservoir, through the opened passageway between the reservoir and chamber, and into the chamber, causing a turbulent flow of liquid into the chamber so as to forcibly sweep air bubbles from the wall of the chamber and the passageway between the reservoir and chamber, and
        when the downward force is removed from the plunger assembly, the planar member moves upward creating a partial vacuum and related negative pressure in the chamber, causing air bubbles remaining in the chamber to expand such that at least some of the bubbles remaining on its walls break loose from the walls and are drawn through the opened passageway into the reservoir, and a resilient actuating assembly which urges the plunger assembly upward in a return stroke when the downward force is removed from the plunger assembly, causing the valve assembly to return to its normally closed position and re-seal the passageway between the reservoir and chamber without applying positive pressure to the chamber; and a vacuum gauge sealably attached to the reservoir, wherein the gauge is disposed in the passageway between the reservoir and chamber, beneath the valve assembly, and wherein a passageway exists between the chamber and gauge which allows the gauge to measure the pressure in the chamber, and hence indicate the moisture content of the soil surrounding the tip.

2. The tensiometer apparatus of claim 1, wherein the lower section of the reservoir tapers inward to form a funnel-shaped lower cavity, and wherein the valve assembly comprises:

a plurality of longitudinal panels which extend from a lower section of a central stem of the plunger assembly, underneath the planar member, wherein, each panel extends radially outward from the stem by the same distance, the radius of the longitudinally lowermost section of each panel steps inward to form a smaller radius extension to each panel, and each panel extension extends radially outward from the stem by the same distance;

a funnel-shaped seal whose exterior shape generally matches the lower cavity of the reservoir, wherein, the outer surface on the bottom of the seal comprises a small bulge such that the bulge contacts the bottom of said cavity, thus providing a primary seal, the section of the seal above the bulge contacts the walls of said cavity, thus providing a secondary seal, the seal comprises an inner hollow cylinder which is open at both the top and bottom ends of the seal, the inner surface on the bottom of the seal comprises a small bulge, the seal is slidably fitted over the smaller radius panel extensions, and the diameter of the seal's inner hollow cylinder is sized to allow the seal to freely slide along the smaller radius panel extensions;

a post which is disposed onto the center of the bottom end of said stem, wherein the post extends below the seal; and a valve bulb which is attached to the bottom of the post, wherein the top section of the valve bulb tapers inward such that it contacts the bulge on the inner surface of the bottom of the seal when the valve assembly is closed, thus providing a seal.

3. The tensiometer apparatus of claim 2, wherein the resilient actuating assembly for urging the plunger assembly upward in a return stroke comprises a compression spring which is slidably fitted over both the longitudinal panels and their smaller radius extensions, and wherein, the spring is located between the horizontal planar member and the seal, the diameter of the spring is sized to allow it to freely slide along the longitudinal panels and their smaller radius extensions, the size and length of the spring, in conjunction with the length of the post, are sized such that the spring pushes downwardly on the top surface of the seal so that the seal is urged against the walls of the lower cavity of the reservoir, and the spring pushes upwardly on the bottom surface of the planar member which urges the valve bulb against the bottom of the seal, resulting in the valve assembly being in its normally closed position, whenever the downward force is applied to the stem, the spring is compressed, the planar member is urged downward towards the seal, and the stem and valve bulb are urged downward causing the valve bulb to move away from the seal, resulting in the valve assembly moving to its open position, and whenever the downward force is removed from the stem, the spring urges the stem and valve bulb upward in a return stroke until the top of the valve bulb makes contact with the bottom of the seal, resulting in the valve assembly returning to its normally closed position.

4. The tensiometer apparatus of claim 3, wherein the plunger assembly is further removably fitted inside the reservoir, and wherein the valve bulb is removably attached to the post, thereby allowing the valve bulb, seal and spring to be easily removed from the plunger assembly for servicing or replacement when damaged or worn.

5. The tensiometer apparatus of claim 3, wherein, the tip is made from any of a variety of rigid, porous, non-corrosive materials that have a bubbling pressure that is greater than normal atmospheric pressure, the tube, reservoir, and plunger assembly except for the seal and spring, are made from any of a variety of rigid, non-corrosive, transparent plastic materials, and the seal is made from any of a variety of flexible but relatively stiff, non-corrosive materials.

6. The tensiometer apparatus of claim 2, wherein the maximum diameter of the valve bulb is sized such that ample space exists between the side surface of the valve bulb and the passageway between the reservoir and chamber so that liquid easily flows through the passageway around the side surface of the valve bulb and down into the chamber when the valve assembly is in its open position.

7. A tensiometer apparatus for measuring the moisture content of soil and other like medium, comprising:

an elongated measurement tube whose interior provides an elongated sealable measurement chamber which is normally filled with liquid;

a porous tip which is sealably attached to the bottom end of the tube, wherein the tip is inserted into the soil and a passageway exists between the chamber and tip which allows liquid in the chamber to flow into the tip;

a reservoir whose bottom end is sealably attached to the top end of the tube, wherein a passageway exists between the reservoir and chamber, and the reservoir is normally filled with liquid;

a piston-type plunger assembly which is slidably fitted inside the reservoir and the passageway between the reservoir and chamber, wherein the plunger assembly comprises, a valve assembly located on the bottom end of the plunger assembly, wherein the valve assembly is normally closed such that the passageway between the reservoir and chamber is normally closed, and wherein whenever a downward force is applied to the plunger assembly it moves downward towards the chamber causing the valve assembly to open such that the passageway between the reservoir and chamber is opened so that liquid in the reservoir is allowed to flow into the chamber to refill the chamber and air which has accumulated in the chamber is allowed to escape into the reservoir, a pump assembly which, whenever the downward force is applied to the plunger assembly, forcibly pumps liquid from the reservoir, through the opened passageway between the reservoir and chamber, into the chamber, causing a turbulent flow of liquid into the chamber which purges air from the chamber by forcibly sweeping air bubbles from its wall, and a resilient actuating assembly which urges the plunger assembly upward in a return stroke when the downward force is removed from the plunger assembly, causing the valve assembly to return to its normally closed position and re-seal the passageway between the reservoir and chamber without applying positive pressure to the chamber;

a vacuum gauge sealably attached to the reservoir, wherein the gauge is disposed in the passageway between the reservoir and chamber, beneath the valve assembly, and wherein a passageway exists between the chamber and gauge which allows the gauge to measure the pressure in the chamber, and hence indicate the moisture content of the soil surrounding the tip; and a cap assembly which is removably attached to the top end of the reservoir, wherein, the cap assembly comprises a cap ring and a flexible but relatively stiff membrane which is sealably attached to the cap ring to form the radially inner section of the cap assembly, wherein the membrane tapers radially upward towards its center to form an actuating button, the cap assembly covers the reservoir and the plunger assembly fitted therein, so as to prevent contamination and evaporation of the liquid contained within the reservoir, the cap assembly can be removed from and re-installed onto the reservoir to allow the reservoir to be easily refilled with liquid, and also to allow the plunger assembly to be easily removed for servicing or replacement when damaged or worn, the length of the upper section of the plunger assembly is sized such that when the cap assembly is attached to the reservoir, a small gap exists between the actuating button and the top of the plunger assembly such that the actuating button normally exerts no force onto the top of the plunger assembly, whenever an external downward force is applied to the top of the actuating button, the membrane flexes downward thereby closing the gap such that the button comes in contact with the top of the plunger assembly and the downward force is transferred to the plunger assembly, causing the plunger assembly to move downward and the valve assembly to open, and whenever the external downward force is removed from the actuating button, the resilient actuating assembly urges the plunger assembly upward in the return stroke causing the membrane to flex upward until the valve assembly returns to the normally closed position and the gap once again exists between the button and the top of the plunger assembly.

8. A tensiometer apparatus for measuring the moisture content of soil and other like medium, comprising:

a measurement tube whose interior provides a sealable measurement chamber which is normally filled with liquid;

a porous tip which is sealably attached to the bottom end of the tube, wherein the tip is inserted into the soil;

a reservoir whose bottom end is sealably attached to the top end of the tube, wherein a passageway exists between the reservoir and chamber, and the reservoir is normally filled with liquid; and a piston-type plunger assembly which is slidably fitted inside the reservoir and passageway, wherein the plunger assembly comprises a pump assembly and liquid flows through the pump assembly in a constricted fashion such that, when a downward force is applied to the plunger assembly the pump assembly moves downward towards the chamber, and when the downward force is removed from the plunger assembly the pump assembly is urged upward in a return stroke by a resilient actuating assembly, wherein the return stroke of the pump assembly creates a partial vacuum and related negative pressure in the chamber which causes air bubbles remaining in the chamber to expand such that at least some of the bubbles remaining on its walls break loose and are drawn into the reservoir, wherein, the pump assembly comprises a horizontal planar member which is oriented perpendicular to the direction of motion of the plunger assembly and has the same shape as the horizontal cross-sectional shape of the interior of the upper section of the reservoir, and which is sized such that it extends close to but slightly short of the interior wall of the upper section of the reservoir, wherein the particular areal size of the planar member is selected to provide a desired level of partial vacuum and related negative pressure in the chamber during the return stroke of the pump assembly.

9. A tensiometer apparatus for measuring the moisture content of soil and other like medium, comprising:

a measurement tube whose interior provides a sealable measurement chamber which is normally filled with liquid;

a porous tip which is sealably attached to the bottom end of the tube, wherein the tip is inserted into the soil;

a reservoir whose bottom end is sealably attached to the top end of the tube, wherein a passageway exists between the reservoir and chamber, and the reservoir is normally filled with liquid; and a piston-type plunger assembly which is slidably fitted inside the reservoir and passageway, wherein the plunger assembly comprises a pump assembly and liquid flows through the pump assembly in a constricted fashion such that, when a downward force is applied to the plunger assembly the pump assembly moves downward towards the chamber, and when the downward force is removed from the plunger assembly the pump assembly is urged upward in a return stroke by a resilient actuating assembly, wherein the return stroke of the pump assembly creates a partial vacuum and related negative pressure in the chamber which causes air bubbles remaining in the chamber to expand such that at least some of the bubbles remaining on its walls break loose and are drawn into the reservoir, wherein, the pump assembly comprises a horizontal planar member which is oriented perpendicular to the direction of motion of the plunger assembly and has the same shape as the horizontal cross-sectional shape of the interior of the upper section of the reservoir, wherein the planar member is perforated and the particular number of perforations and their size is selected to provide a desired level of partial vacuum and related negative pressure in the chamber during the return stroke of the pump assembly.

10. A tensiometer apparatus for measuring the moisture content of soil and other like medium, comprising:
   a measurement tube whose interior provides a sealable measurement chamber which is normally filled with liquid;
   a porous tip which is sealably attached to the bottom end of the tube, wherein the tip is inserted into the soil;
   a reservoir whose bottom end is sealably attached to the top end of the tube, wherein a passageway exists between the reservoir and chamber, and the reservoir is normally filled with liquid; and
   a piston-type plunger assembly which is slidably fitted inside the reservoir and passageway, wherein the plunger assembly comprises a pump assembly and liquid flows through the pump assembly in a constricted fashion such that,
      when a downward force is applied to the plunger assembly the pump assembly moves downward towards the chamber, and
      when the downward force is removed from the plunger assembly the pump assembly is urged upward in a return stroke by a resilient actuating assembly, wherein the return stroke of the pump assembly creates a partial vacuum and related negative pressure in the chamber which causes air bubbles remaining in the chamber to expand such that at least some of the bubbles remaining on its walls break loose and are drawn into the reservoir, wherein,
   the pump assembly comprises a horizontal planar member which is oriented perpendicular to the direction of motion of the plunger assembly and has the same shape as the horizontal cross-sectional shape of the interior of the upper section of the reservoir, and which is sized such that it extends close to but slightly short of the interior wall of the upper section of the reservoir, wherein the planar member is perforated, and wherein the particular number of perforations and their size, in conjunction with the particular areal size of the planar member, are selected to provide a desired level of partial vacuum and related negative pressure in the chamber during the return stroke of the pump assembly.

11. A process for measuring the moisture content of soil and other like medium using a tensiometer, comprising the process actions of:
   inserting a porous tip of the tensiometer, which is located on the bottom of a measurement chamber of the tensiometer, into the soil;
   pouring liquid into a reservoir of the tensiometer which is located on the top of the measurement chamber, wherein a spring-loaded piston-type plunger assembly is slidably fit into the reservoir, and wherein the plunger assembly comprises a sealing assembly which seals a passageway from the reservoir to the chamber;
   depressing the plunger assembly downward to open the passageway from the reservoir to the measurement chamber, such that the liquid flows from the reservoir into the chamber;
   once the liquid level in the measurement chamber rises above a passageway from the chamber to a vacuum gauge of the tensiometer, releasing the plunger assembly which moves it upward in a return stroke, wherein the upward motion of the plunger assembly creates a partial vacuum and related negative pressure in the chamber, thus causing bubbles remaining in the chamber to expand such that at least some of the bubbles remaining on the chamber wall break loose from the wall and are drawn into the reservoir, and when the plunger assembly completes its return stroke the passageway from the reservoir to the chamber is re-sealed without applying a positive pressure to the chamber;
   periodically reading a current negative pressure in the measurement chamber on the gauge, wherein the negative pressure is caused by liquid attempting to flow out of the chamber through the porous tip into the soil;
   based on a prescribed measurement chamber refill service interval, depressing the plunger assembly downward to open the passageway from the reservoir to the chamber such that,
      liquid flows from the reservoir into the chamber to refill the chamber,
      air which has accumulated in the chamber escapes into the reservoir, and
      a turbulent flow of liquid into the chamber is generated by the downward motion of a disc on the plunger assembly which forcibly sweeps away bubbles remaining on the chamber walls; and
   releasing the plunger assembly to move upward in a return stroke, wherein the upward motion of the disc on the plunger assembly creates a partial vacuum and related negative pressure in the measurement chamber, thus causing bubbles remaining in the chamber to expand such that at least some of the bubbles remaining on the chamber wall break loose from the wall and are drawn into the reservoir, and when the plunger assembly completes its return stroke the passageway from the reservoir to the chamber is re-sealed without applying a positive pressure to the chamber.

12. The process of claim 11, wherein the process actions of depressing the plunger assembly and releasing the plunger assembly are repeated until bubbles no longer remain on the chamber wall.

* * * * *